(12) United States Patent
MacKeigan et al.

(10) Patent No.: US 9,221,760 B2
(45) Date of Patent: Dec. 29, 2015

(54) AUTOPHAGY INHIBITORS

(75) Inventors: Jeffrey Paul MacKeigan, East Grand Rapids, MI (US); Katie Renee Martin, Minneapolis, MN (US); Megan Lynne Goodall, Jackson, MI (US); Stephen Gately, Scottsdale, AZ (US); Tong Wang, Scottsdale, AZ (US)

(73) Assignees: VAN ANDEL RESEARCH INSTITUTE, Grand Rapids, MI (US); TRANSLATIONAL GENOMICS RESEARCH INSTITUTE, Phoenix, AZ (US)

( * ) Notice: Subject to any disclaimer, the term of this patent is extended or adjusted under 35 U.S.C. 154(b) by 0 days.

(21) Appl. No.: 14/116,650

(22) PCT Filed: May 9, 2012

(86) PCT No.: PCT/US2012/037158
§ 371 (c)(1),
(2), (4) Date: Feb. 12, 2014

(87) PCT Pub. No.: WO2012/154879
PCT Pub. Date: Nov. 15, 2012

(65) Prior Publication Data
US 2014/0148451 A1    May 29, 2014

Related U.S. Application Data

(60) Provisional application No. 61/483,991, filed on May 9, 2011.

(51) Int. Cl.
| C07D 219/10 | (2006.01) |
| C07D 471/04 | (2006.01) |
| C07D 219/12 | (2006.01) |
| C07D 221/16 | (2006.01) |
| C07D 401/12 | (2006.01) |
| C07D 219/08 | (2006.01) |

(52) U.S. Cl.
CPC ............ *C07D 219/10* (2013.01); *C07D 219/08* (2013.01); *C07D 219/12* (2013.01); *C07D 221/16* (2013.01); *C07D 401/12* (2013.01); *C07D 471/04* (2013.01)

(58) Field of Classification Search
CPC ... C07D 471/04; C07D 219/08; C07D 401/02
USPC .................... 546/81, 106; 514/292
See application file for complete search history.

(56) References Cited

U.S. PATENT DOCUMENTS

| 4,107,288 A | 8/1978 | Oppenheim et al. |
| 4,999,358 A * | 3/1991 | Martin et al. ............... 514/297 |
| 5,145,684 A | 9/1992 | Liversidge et al. |
| 5,149,813 A | 9/1992 | Martin et al. |
| 5,294,715 A | 3/1994 | Papadopoulou-Rosenzweig et al. |
| 5,300,517 A | 4/1994 | Hasegawa et al. |
| 5,886,185 A | 3/1999 | Chou et al. |
| 5,939,428 A | 8/1999 | Su et al. |
| 7,442,507 B2 | 10/2008 | Polsky et al. |
| 7,605,265 B2 | 10/2009 | Ip et al. |
| 2002/0169183 A1 | 11/2002 | Villar et al. |
| 2008/0161324 A1 | 7/2008 | Johansen et al. |
| 2010/0063027 A1 | 3/2010 | Okuno et al. |
| 2010/0093004 A1 | 4/2010 | Patton et al. |
| 2010/0112012 A1 | 5/2010 | Gudkov et al. |
| 2010/0267945 A1 | 10/2010 | Okuno et al. |
| 2010/0273841 A1 | 10/2010 | Okuno et al. |
| 2010/0273842 A1 | 10/2010 | Okuno et al. |

FOREIGN PATENT DOCUMENTS

| DE | 360421 | * | 10/1922 |
| DE | 4444045 C3 | | 3/1927 |
| EP | 446604 A2 | | 9/1991 |
| GB | 600851 | | 4/1948 |
| JP | 01-221364 A | | 4/1989 |
| WO | 9102725 | * | 3/1991 |
| WO | WO95/02397 A1 | | 1/1995 |
| WO | WO96/39818 A1 | | 12/1996 |
| WO | WO97/27179 A2 | | 7/1997 |
| WO | WO98/54148 A2 | | 3/1998 |

(Continued)

OTHER PUBLICATIONS

Rastogi Shri Nivas et al , Caplus abstract DN 108:179601, 1987.*

(Continued)

*Primary Examiner* — Rita Desai
(74) *Attorney, Agent, or Firm* — Honigman Miller Schwartz and Cohn LLP; Douglas H. Siegel; Jonathan P. O'Brien

(57) ABSTRACT

The present invention relates to compounds of formulas III and V that are useful as pharmaceutical agents, particularly as autophagy inhibitors.

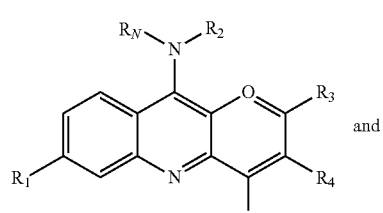

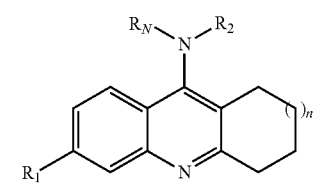

1 Claim, 6 Drawing Sheets

(56) References Cited

FOREIGN PATENT DOCUMENTS

| WO | WO99/58126 A1 | 11/1999 |
|---|---|---|
| WO | WO99/64054 A1 | 12/1999 |
| WO | WO00/32175 A2 | 6/2000 |
| WO | WO2007/122274 A1 | 11/2007 |
| WO | WO2010/130147 A1 | 11/2010 |

OTHER PUBLICATIONS

Sargent et al. 1946 Attempts to find new Antimalarials.*
Steinburg et al. 1975, A Hydrophobic Binding site in Acetycholinesterase.*
Yamato et al 1989 1989, Synthesis and Antitumor activity of Fused Tetracyclic Quinoline Derivatives.*
Sargent Lewis et al, 1947, Studies in the Acridine Series.*
Rastogi Shri Nivas et al , 1987.*
Thuy Nguyen et al , 2011, Anti-prion activities and drug-like potential of functionalozed quinacrine analogs with basic residues at the 9-amino position.*
Zhurnal Obshchei Khimii (1937), 7, 842-52 , Acridine compounds as a sourse of medicinal products III Tetrahydro compounds.*
Chandra, T., et al., "Synthesis of Substituted Acridinyl Pyrazoline Derivatives and Their Evaluation for Anti-Inflammatory Activity", European Journal of Medicinal Chemistry, 2010, pp. 1772-1776, vol. 45.
PCT International Search Report for PCT/US2012/037158, dated Aug. 7, 2012.
Amaravadi, RK, et al. Autophagy inhibition enhances therapy-induced apoptosis in a Myc-induced model of lymphoma. J Clin Invest 2007; 117:326-36.
Anderson, T. et al. How can we identify parasite genes that underlie antimalarial drug resistance? Pharmacogenomics 2011; 12:59-85.
Apel, A., et al. Blocked autophagy sensitizes resistant carcinoma cells to radiation therapy. Cancer Res 2008; 68:1485-94.
Armstrong, JL, et al. Oncogenic B-RAF signaling in melanoma impairs the therapeutic advantage of autophagy inhibition. Clin Cancer Res 2011; 17:2216-26.
Boya, P., et al. Inhibition of macroautophagy triggers apoptosis. Mol Cell Biol 2005; 25:1025-40.
Chen, B. et al. BRAFV600E negatively regulates the AKT pathway in melanoma cell lines. PLoS One 2012; 7:e42598.
Chou, T.C. Drug combination studies and their synergy quantification using the Chou-Talalay method. Cancer Res 2010; 70:440-6.
Corazzari, M., et al. Harnessing Autophagy for Melanoma Benefit. Cell Biology: Res Ther2013; 2:1.
Corse, J., et al. N-Substituted 2-Methoxy-6-chloro-9-aminoacridines Derived from Unsymmetrical Aliphatic AminesI. Journal of the American Chemical Society (1946), 68, 1905-1910.
Davies, H., et al., Mutations of the BRAF gene in human cancer. Nature (2002) 417:949-954.
De, D, et al, Structure-activity relationships for antiplasmodial activity among 7-substituted 4-aminoquinolines. J Med Chem 1998; 41:4918-26.
Degenhardt, K., et al., Autophagy promotes tumor cell survival and restricts necrosis, inflammation, and tumorigenesis. Cancer Cell 10, 51-64 (2006).
Fan, Q.W., et al. AKT and autophagy cooperate to promote survival of drug-resistant glioma. Sci Signal 2010; 3 (147): :ra81.
Fitzgibbons, P. et al. Prognostic factors in breast cancer. College of American Pathologists Consensus Statement 1999. Arch. Pathol. Lab. Med. 124:966-78, 2000.
Flaherty, KT, et al. From genes to drugs: targeted strategies for melanoma. Nat Rev Cancer 2012; 12:349-61.
Flaherty, KT, et al. Inhibition of mutated, activated BRAF in metastatic melanoma. N Engl J Med 2010; 363:809-819.
Foley, M. et al. Quinoline antimalarials: mechanisms of action and resistance and prospects for new agents. Pharmacol Ther 1998; 79:55-87.
Guo, J.Y., et al. Activated Ras requires autophagy to maintain oxidative metabolism and tumorigenesis. Genes Dev 2011; 25:460-70.
Han, W., et al. Autophagy inhibition enhances daunorubicin-induced apoptosis in K562 cells. PLoS One 2011; 6:12, e28491.
Han, W., et al. EGFR tyrosine kinase inhibitors activate autophagy as a cytoprotective response in human lung cancer cells. PLoS One 2011; 6:6, e18691.
Hiss, D.C., et al.. Combination of tunicamycin with anticancer drugs synergistically enhances their toxicity in multidrug-resistant human ovarian cystadenocarcinoma cells. Cancer Cell Int 2007; 7:5.
Iwaniuk, D.P., et al. Synthesis and antimalarial activity of new chloroquine analogues carrying a multifunctional linear side chain. Bioorg Med Chem 2009; 17:6560-6.
Janku, F., et al. Autophagy as a target for anticancer therapy. Nat Rev Clin Oncol 2011; 8:528-39.
Jin, S, et al., Role of autophagy in cancer: management of metabolic stress, Autophagy 3:1, 28-31 (2007).
Karantza-Wadsworth V., et al. Autophagy mitigates metabolic stress and genome damage in mammary tumorigenesis. Genes Dv 21:1621-1635 (2007).
Kimura, S., et al. Dissection of the autophagosome maturation process by a novel reporter protein, tandem fluorescent-tagged LC3. Autophagy 2007; 3:5, 452-60.
Kitchen, S.E., et al. The intercalation of 6-chloro-2-substituted-9-[[3-(dimethylamino)propyl]amino]acridines with DNA. J. Med. Chem. 1985, 28(7), 940-944.
Klionsky, DJ. Autophagy: from phenomenology to molecular understanding in less than a decade. Nat Rev Mol Cell Biol (2007) 8, 931-937.
Klionsky, DJ, et al. Guidelines to the use and interpretation of assays for monitoring autophagy. Autophagy 2012; 8:4, 445-544.
Kohli, L. et al. Autophagy: cerebral home cooking. Am J Pathol 2010; 176(3):1065-71.
Kondo, Y. et al. The role of autophagy in cancer development and response to therapy. Nat Rev Cancer 2005; 5:726-34.
Levine, B., et al., Autophagy in the pathogenesis of disease, Cell 132, 27-42 (2008).
Li, DD, et al. The Inhibition of Autophagy Sensitises Colon Cancer Cells with Wild-Type p53 but Not Mutant p53 to Topotecan Treatment. PLoS One 2012; 7(9):e45058.
Liu, B., et al. Autophagic pathways as new targets for cancer drug development. Acta Pharmacol Sin 2010; 31:1154-1164.
Loeb, RF. Activity of a new antimalarial agent, chloroquine (SN7618). JAMA 1946; 130:1069-70.
Ma, X.H., et al. Measurements of tumor cell autophagy predict invasiveness, resistance to chemotherapy, and survival in melanoma. Clin Cancer Res 2011; 17:3478-89.
Maddodi, N. et al. Induction of autophagy and inhibition of melanoma growth in vitro and in vivo by hyperactivation of oncogenic BRAF. J Invest Dermatol 2010; 130:1657-67.
Martin, K.R., et al. Computational model for autophagic vesicle dynamics in single cells. Autophagy 2013; 9(1):74-92.
Mathew R., et al, Role of autophagy in cancer, Nat Rev Cancer 7, 961-967 (2007).
Mathew R., et al. Autophagy, stress, and cancer metabolism: what doesn't kill you makes you stronger. Cold Spring Harb Symp Quant Biol 2011; 76:389-96.
Mathew R., et al., Autophagy suppresses tumor progression by limiting chromosomal instablity. Genes Dv 21:1367-1381 (2007).
McAfee, Q., et al, Autophagy inhibitor Lys05 has single-agent antitumor activity and reproduces the phenotype of a genetic autophagy deficiency. PNAS (2012) 109(21):8253-8258.
Mizushima, N, et al. Autophagy fights disease through cellular self-digestion. Nature 2008; 451(7182):1069-1075.
Morselli, E., et al. Anti- and pro-tumor functions of autophagy. Biochim Biophys Acta 2009; 1793:1524-32.
Rao, R., et al. Combination of pan-histone deacetylase inhibitor and autophagy inhibitor exerts superior efficacy against triple-negative human breast cancer cells. Mol Cancer Ther 2012; 11:973-83.
Rosenfeldt, M.T., et al. The role of autophagy in tumour development and cancer therapy. Expert Rev Mol Med 2009; 11:e36.
Ross, J.S., et al. The HER-2/neu gene and protein in breast cancer 2003: biomarker and target of therapy. The Oncologist 8:307-25, 2003.

(56) References Cited

OTHER PUBLICATIONS

Sharma, N., et al. Inhibition of autophagy and induction of breast cancer cell death by mefloquine, an antimalarial agent. Cancer Lett 2012; 326:143-54.
Parker, R.M., et al. mRNA: detection by In Situ and northern hybridization. Methods in Molecular Biology 106:247-283 (1999).
Sheen, JH., et al. Defective regulation of autophagy upon leucine deprivation reveals a targetable liability of human melanoma cells in vitro and in vivo. Cancer Cell 2011; 19:613-28.
Sasaki, K., et al Chloroquine potentiates the anti-cancer effect of 5-fluorouracil on colon cancer cells. BMC Cancer 2010; 10:370.
Shingu, T., et al Stage-specific effect of inhibition of autophagy on chemotherapy-induced cytotoxicity. Autophagy 2009; 5:4, 537-539.
Simonsen, A., et al. Coordination of membrane events during autophagy by multiple class III PI3-kinase complexes. J Cell Biol 2009; 186:773-82.
Singh, R., et al. Autophagy regulates lipid metabolism. Nature 2009; 458:1131-1135.
Solomon, V.R., et al. Design and synthesis of chloroquine analogs with anti-breast cancer property. Eur J Med Chem 45 (2010) 3916-3923.
Solomon, VR, et al. Chloroquine and its analogs: a new promise of an old drug for effective and safe cancer therapies. Eur J Pharmacol 2009; 625:220-33.
Sotelo, J., et al. Adding chloroquine to conventional treatment for glioblastoma multiforme: a randomized, double-blind, placebo-controlled trial. Ann Intern Med 2006; 144(5):337-43.
Velikkakath, AK, et al. Mammalian Atg2 proteins are essential for autophagosome formation and important for regulation of size and distribution of lipid droplets. Mol Biol Cell 2012; 23:896-909.
Wang, et al. Linker-modified triamine-linked acridine dimers: Synthesis and cytotoxicity properties in vitro and in vivo. Bioorganic & Medicinal Chemistry (2007), 15(2) 735-748.
White, E. Deconvoluting the context-dependent role for autophagy in cancer. Nat Rev Cancer 2012; 12:401-10.
Wu, W.K., et al. The autophagic paradox in cancer therapy. Oncogene 2012; 31:939-53.
Wu, Y.C., et al. Inhibition of macroautophagy by bafilomycin A1 lowers proliferation and induces apoptosis in colon cancer cells. Biochem Biophys Res Commun 2009; 382:451-6.
Xie, X., et al. Coordinate autophagy and mTOR pathway inhibition enhances cell death in melanoma. PLoS One 2013; 8:e55096XIE, X., et al. Coordinate autophagy and mTOR pathway inhibition enhances cell death in melanoma. PLoS One 2013; 8:e55096.
Xu, Y., et al. Inhibition of autophagy enhances cisplatin cytotoxicity through endoplasmic reticulum stress in human cervical cancer cells. Cancer Lett 2012; 314:232-43.
Yan, H, et al. A formal model for analyzing drug combination effects and its application in TNF-alpha-induced NFkappaB pathway. BMC Syst. Biol. 2010; 4:50.
Yang, S., et al. Pancreatic cancers require autophagy for tumor growth. Genes Dev 2011; 25:717-29.
Yang, Z., et al. Eaten alive: a history of macroautophagy. Nat Cell Biol 2010; 12:814-22.
Berge, S.M., et al. Pharmaceutical salts. J. Pharm. Sci. (1977) 66(1), 1.
Burrows, J.N., et al. Designing the next generation of medicines for malaria control and eradictation. Malar J. Jun. 6, 2013; 12:187. doi 10.1186/1475-2875-12-187.
Gould, P.L. Salt selection for basic drugs. Int. J. Pharm., 33 (1986) 201-217.
Hod, A simplified ribonuclease protection assay. Biotechniques 13(6):852-854 (1992).
Jensen, M., et al. Seventy-five years of Resochin in the fight against Malaria. Parasitol Res Sep. 2009; 105(3) 609-27. doi: 10.1007/s00436-009-1524-8.
Jin, S., et al. Tumor suppression by autophagy through the management of metabolic stress. Autophagy 2008 4 (5):563-566.
Muregi, F.W., et al. Novel drug targets in malaria parasite with potential to yield antimalarial drugs with long useful therapeutic lives. Curr Pharm Des 2012; 18:3505-3521.
Weis et al., Detection of rare mRNAs via quantitative RT-PCT. Trends in Genetics vol. 8(8):263-264 (1992).
National Library of Medicine US Clinical trial NCT01575782 investigating chloroquine as an anti-autophagic radiosensitizing drug in stage I-III small cell lung cancer received by FDA Apr. 3, 2012; clinicaltrials.gov: Bethesda, MD, 2013.
National Library of Medicine US Clinical trial NCT00969306 investigating chloroquine as an anti-autophagy drug in stage IV small cell lung cancer (SCLC) Patients (Chloroquine IV) received by FDA Aug. 31, 2009; clinicaltrials.gov: Bethesda, MD, 2013.
National Library of Medicine US Clinical trial NCT01446016 investigating chloroquine taxane chemotherapy for advanced or metastatic breast cancer patients who have filed an anthracycline (CAT) received by FDA Sep. 29, 2011; clinicaltrials.gov: Bethesda, MD, 2013.
National Library of Medicine US Clinical trial NCT01023477 study of the efficacy of chloroquine in the treatment of ductal carcinoma in situ (the PINC Trial) received by FDA Dec. 1, 2009; clinicaltrials.gov: Bethesda, MD, 2013.
National Library of Medicine US Clinical trial NCT01469455 study of DNA repair inhibitor & irradiation on melanoma (DRIIM) received by FDA Oct. 24, 2011; clinicaltrials.gov: Bethesda, MD, 2013.
National Library of Medicine US Clinical trial NCT01438177 study of chloroquine in combination with VELCADE and cyclophosphamide for relapsed and refractory multiple myeloma received by FDA Sep. 8, 2011; clinicaltrials.gov: Bethesda, MD, 2013.
National Library of Medicine US Clinical trial NCT01727531 study of IDO2 genetic status informs the neoadjuvant efficacy of chloroquine (CQ) in brain metastasis radiotherapy received by FDA Nov. 7, 2012; clinicaltrials.gov: Bethesda, MD, 2013.
National Library of Medicine US Clinical trial NCT00224978 study of chloroquine for treatment of glioblastoma multiforme received by FDA Sep. 21, 2005; clinicaltrials.gov: Bethesda, MD, 2013.
National Library of Medicine US Clinical trial NCT01273805 study of hydroxychloroquine in previously treated patients with metastatic pancreatic cancer received by FDA Jan. 7, 2011; clinicaltrials.gov: Bethesda, MD, 2013.
National Library of Medicine US Clinical trial NCT00933803 study of hydroxychloroquine + carboplatin, paclitaxel and bevacizumab in non-small cell lung cancer (NSCLC) received by FDA Jun. 16, 2008; clinicaltrials.gov: Bethesda, MD, 2013.
National Library of Medicine US Clinical trial NCT01006369 study of hydroxychloroquine, capecitabine, oxaliplatin, and bevacizumab in treating patients with metastatic colorectal cancer received by FDA Oct. 30, 2009; clinicaltrials.gov: Bethesda, MD, 2013.
National Library of Medicine US Clinical trial NCT01480154 study of Akt inhibitor MK2206 and hydroxychloroquine in treating patients with advanced solid tumors, melanoma, prostate or kidney cancer received by FDA Nov. 23, 2011; clinicaltrials.gov: Bethesda, MD, 2013.
National Library of Medicine US Clinical trial NCT00765765 study of ixabepilone and hydroxychloroquine in treating patients with metastatic breast cancer received by FDA Oct. 2, 2008; clinicaltrials.gov: Bethesda, MD, 2013.
National Library of Medicine US Clinical trial NCT00728845 study of hydroxychloroquine, carboplatin, paclitaxel, and bevacizumab in recurrent advanced non-small cell lung cancer received by FDA Aug. 5, 2008; clinicaltrials.gov: Bethesda, MD, 2013.
National Library of Medicine US Clinical trial NCT01266057 study of sirolimus or vorinostat and hydroxychloroquine in advanced cancer received by FDA Dec. 22, 2010; clinicaltrials.gov: Bethesda, MD, 2013.
National Library of Medicine US Clinical trial NCT00813423 study of sunitinib malate and hydroxychloroquine in treating patients with advanced solid tumors that have no responded to chemotherapy received by FDA Dec. 20, 2008; clinicaltrials.gov: Bethesda, MD, 2013.

(56) References Cited

OTHER PUBLICATIONS

National Library of Medicine US Clinical trial NCT01494155 study of short course radiation therapy with proton or photon beam capecitabine and hydroxychloroquine for resectable pancreatic cancer received by FDA Jul. 29, 2011; clinicaltrials.gov: Bethesda, MD, 2013.
National Library of Medicine US Clinical trial NCT01023737 study of hydroxychloroquine + vorinostat in advanced solid tumors received by FDA Jul. 22, 2009; clinicaltrials.gov: Bethesda, MD, 2013.
National Library of Medicine US Clinical trial NCT00786682 study of docetaxel and hydroxychloroquine in treating patients with metastatic prostate cancer received by FDA Nov. 5, 2008; clinicaltrials.gov: Bethesda, MD, 2013.
National Library of Medicine US Clinical trial NCT00726596 study of hydroxychloroquine in treating patients with rising PSA levels after local therapy for prostate cancer received by FDA Jul. 31, 2008; clinicaltrials.gov: Bethesda, MD, 2013.
National Library of Medicine US Clinical trial NCT01417403 study of hydroxychloroquine in treating patients with solid tumors undergoing radiation therapy for bone metastases received by FDA Aug. 10, 2011; clinicaltrials.gov: Bethesda, MD, 2013.
National Library of Medicine US Clinical trial NCT00809237 study of hydroxychloroquine and gefitinib to treat lung cancer received by FDA Dec. 16, 2008; clinicaltrials.gov: Bethesda, MD, 2013.
National Library of Medicine US Clinical trial NCT00909831 study of hydroxychloroquine and temsirolimus in treating patients with metastatic solid tumors that have not responded to treatment received by FDA May 28, 2009; clinicaltrials.gov: Bethesda, MD, 2013.
National Library of Medicine US Clinical trial NCT00714181 study of hydroxychloroquine and temozolomide in treating patients with metastatic or unresectable solid tumors received by FDA Jul. 11, 2008, clinicaltrials.gov: Bethesda, MD, 2013.
National Library of Medicine US Clinical trial NCT01206530 study of FOLFOX/Bevacizumab/hydroxychloroquine (HCQ) in colorectal cancer received by FDA Sep. 16, 2010, clinicaltrials.gov: Bethesda, MD, 2013.
National Library of Medicine US Clinical trial NCT01026844 study of hydroxychloroquine with or without erlotinib in advanced non-small cell lung cancer (NSCLC) received by FDA Dec. 2, 2009, clinicaltrials.gov: Bethesda, MD, 2013.
National Library of Medicine US Clinical trial NCT00486603 study of hydroxychloroquine, radiation therapy, and temozolomide in treating patients with newly diagnosed glioblastoma multiforme received by FDA Jun. 13, 2007, clinicaltrials.gov: Bethesda, MD, 2013.
National Library of Medicine US Clinical trial NCT01649947 study of modulation of autophagy in patients with advanced/recurrent non-small cell lung cancer—phase II received by FDA Jul. 20, 2012, clinicaltrials.gov: Bethesda, MD, 2013.
National Library of Medicine US Clinical trial NCT00977470 study of erlotinib with or without hydroxychloroquine in chemo-naive advanced NSCLC and (EGFR) mutations received by FDA Sep. 11, 2009, clinicaltrials.gov: Bethesda, MD, 2013.
National Library of Medicine US Clinical trial NCT01506973 study of a phase I/II/Pharmacodynamic study of hydroxychloroquine in combination with gemcitabine/abraxane to inhibit autophagy in pancreatic cancer received by FDA Jan. 3, 2012, clinicaltrials.gov: Bethesda, MD, 2013.
National Library of Medicine US Clinical trial NCT01128296 study of pre-surgery gemcitabine + hydroxychloroquine (GcHc) in Stage IIb or III adenocarcinoma of the pancreas received by FDA May 20, 2010, clinicaltrials.gov: Bethesda, MD, 2013.
National Library of Medicine US Clinical trial NCT00568880 study of hydroxychloroquine and bortezomib in treating patients with relapsed or refractory multiple myeloma received by FDA Dec. 5, 2007, clinicaltrials.gov: Bethesda, MD, 2013.
National Library of Medicine US Clinical trial NCT01144169 study of hydroxychloroquine before surgery in patients with primary renal cell carcinoma received by FDA Jun. 10, 2010, clinicaltrials.gov: Bethesda, MD, 2013.
National Library of Medicine US Clinical trial NCT00962845 study of hydroxychloroquine in patients with stage III or stage IV melanoma that can be removed by surgery received by FDA Aug. 19, 2009, clinicaltrials.gov: Bethesda, MD, 2013.
National Library of Medicine US Clinical trial NCT01292408 study of autophagy inhibition using hydroxychloroquine in breast cancer patients received by FDA Dec. 15, 2010, clinicaltrials.gov: Bethesda, MD, 2013.
National Library of Medicine US Clinical trial NCT01689987 study of hydroxychloroquine, cyclophosphamide, dexamethasone, and sirolimus in treating patients with relapsed or refratory multiple myeloma received by FDA Sep. 17, 2012, clinicaltrials.gov: Bethesda, MD, 2013.
National Library of Medicine US Clinical trial NCT01550367 study of hydroxychloroquine and aldesleukin in renal cell carcinoma patients (RCC) received by FDA Feb. 29, 2012, clinicaltrials.gov: Bethesda, MD, 2013.
National Library of Medicine US Clinical trial NCT01396200 study of cyclophosphamide and pulse dexamethasone with rapamycin or hydroxychloroquine received by FDA Jul. 14, 2011, clinicaltrials.gov: Bethesda, MD, 2013.
National Library of Medicine US Clinical trial NCT01227135 study of imatinib mesylate with or without hydroxychloroquine in treating patients with chronic myeloid leukemia received by FDA Oct. 21, 2010, clinicaltrials.gov: Bethesda, MD, 2013.
National Library of Medicine US Clinical trial NCT01602588 study of a randomised trial investigating the additional benefit of hydroxychloroquine (HCQ) to short course radiotherapy (SCRT) in patients aged 70 years and older with high grade gliomas (HGG) received by FDA May 8, 2012, clinicaltrials.gov: Bethesda, MD, 2013.
National Library of Medicine US Clinical trial NCT01510119 study of autophagy inhibition to augment mTOR inhibition: A phase I/II trial of RAD001 and hydroxychloroquine in patients with previously treated renal cell carcinoma received by FDA Jan. 11, 2012, clinicaltrials.gov: Bethesda, MD, 2013.
National Library of Medicine US Clinical trial NCT00031824 study of hydroxychloroquine in treating patients with newly diagnosed chronic graft-versus-host diseases received by FDA Mar. 8, 2002, clinicaltrials.gov: Bethesda, MD, 2013.
National Library of Medicine US Clinical trial NCT01548768 study of RHYTHM (Formerly escape II myocardium) received by FDA Mar. 6, 2012, clinicaltrials.gov: Bethesda, MD, 2013.
National Library of Medicine US Clinical trial NCT00908089 study of TNF-blocking therapy in combination with disease-modifying antirheumatic drugs in early rheumatoid arthritis (NEO-RACo) received by FDA May 22, 2009, clinicaltrials.gov: Bethesda, MD, 2013.
National Library of Medicine US Clinical trial NCT01687179 safety study of sirolimus and hydroxychloroquine in women with lymphangioleiomyomatosis (SAIL) received by FDA Aug. 2, 2012, clinicaltrials.gov: Bethesda, MD, 2013.
National Library of Medicine US Clinical trial NCT00405275 study of rheumatoid arthritis: comparison of active therapies in patients with active disease despite methotrexate therapy (RACAT) received by FDA Nov. 29, 2006, clinicaltrials.gov: Bethesda, MD, 2013.
National Library of Medicine US Clinical trial NCT00771056 study of hydroxychloroquine in untreated B-CLL patients received by FDA Oct. 8, 2008, clinicaltrials.gov: Bethesda, MD, 2013.
National Library of Medicine US Clinical trial NCT01709578 to evaluate the effect of SAR153191 (REGN88) added to other RA drugs in patients with RA who are not responding to or intolerant of anti-TNF therapy (SARIL-RA-TARGET) received by FDA Oct. 15, 2012, clinicaltrials.gov: Bethesda, MD, 2013.

\* cited by examiner

A

B

AUTOPHAGY INHIBITORS

CROSS REFERENCE TO RELATED APPLICATIONS

This application is a 35 U.S.C. §371 United States National Phase Application of, and claims priority to, PCT International Application No. PCT/US2012/037158 filed May 9, 2012, which claims the benefit under 35 U.S.C. §119 of U.S. Provisional Application Ser. No. 61/483,991 filed on May 9, 2011. The entire contents of both of the aforesaid applications are incorporated by reference herein in their entireties.

FIELD OF THE INVENTION

The present invention relates to compounds that are useful as pharmaceutical agents, particularly as autophagy inhibitors.

BACKGROUND OF THE INVENTION

Macroautophagy (autophagy) is an important mechanism for targeting cellular components including proteins, protein aggregates, and organelles for degradation in lysosomes. This catabolic, cellular self-digestion process is induced in response to starvation or stress, causing the formation of double membrane vesicles called autophagosomes that engulf proteins and organelles. Autophagosomes then fuse with lysosomes where the autophagosome and their cargo are degraded. This lysosome-mediated cellular self-digestion serves to recycle intracellular nutrients to sustain cell metabolism during starvation and to eliminate damaged proteins and organelles that accumulate during stress. Although elimination of individual proteins occurs by the ubiquitin-mediated proteasome degradation pathway, the autophagy pathway can eliminate protein aggregates and organelles. Thus, autophagy complements and overlaps with proteasome function to prevent the accumulation of damaged cellular components during starvation and stress. Through these functions, autophagy is an essential cellular stress response that maintains protein and organelle quality control, protects the genome from damage, and sustains cell and mammalian viability.

Autophagy is controlled by ATG proteins, initially identified in yeast, for which there are mammalian homologues (Levine, B., and Kroemer, G. (2008), Autophagy in the pathogenesis of disease, Cell 132, 27-42). ATG proteins are comprised of kinases, proteases, and two ubiquitin-like conjugation systems that likely function in concert with a host of unknown cellular proteins to control autophagosome formation, cargo recognition, engulfment, and trafficking to lysosomes.

Autophagy dysfunction is a major contributor to diseases including, but not limited to, neurodegeneration, liver disease, and cancer. Many human neurodegenerative diseases are associated with aberrant mutant and/or polyubiquitinated protein accumulation and excessive neuronal cell death.

Autophagy is also induced by stress and starvation in tumor cells, where it predominantly provides a prosurvival function. Metabolic stress is common, and autophagy localizes to metabolically-stressed tumor regions. Autophagy has been identified as an important survival pathway in epithelial tumor cells that enables long-term survival to metabolic stress (Degenhardt, K., et al. (2006), Autophagy promotes tumor cell survival and restricts necrosis, inflammation, and tumorigenesis, Cancer Cell 10, 51-64; Jin, S., and White, E. (2007), Role of autophagy in cancer: management of metabolic stress. Autophagy 3, 28-31; Karantza-Wadsworth, V., et al., (2007), Autophagy mitigates metabolic stress and genome damage in mammary tumorigenesis, Genes Dev 21, 1621-1635; Mathew, R. et al., (2007a), Role of autophagy in cancer, Nat Rev Cancer 7, 961-967; Mathew, R., et al. (2007b), Autophagy suppresses tumor progression by limiting chromosomal instability, Genes Dev 21, 1367-1381). Tumor cells with defined defects in autophagy accumulate p62-containing protein aggregates, damage DNA, and die in response to stress, whereas those with intact autophagy can survive for weeks, utilizing the autophagy survival pathway. Thus, autophagy prevents tumor cell damage and maintains metabolism. Tumor cells exploit this survival function to remain dormant, only to reemerge under more favorable conditions.

Paradoxically, autophagy defects through allelic loss of the essential autophagy gene beclin1 or through constitutive activation of the autophagy-suppressing PI-3 kinase/mTOR pathway are common in human tumors. Roughly half of human cancers may have impaired autophagy, either due to constitutive activation of the PI-3 kinase pathway or allelic loss of the essential autophagy gene beclin1, rendering them particularly susceptible to metabolic stress and autophagy inhibition (Jin et al., 2007; Jin, S., and White, E. (2008).

The importance of autophagy in cellular garbage disposal is clear, since autophagy is the only identified mechanism for the turnover of large cellular structures, such as organelles and protein aggregates. How organelles are recognized and directed to autophagosomes for degradation may involve organelle-specific processes, such as mitophagy and ER-phagy, that may mitigate oxidative stress emanating from dysfunctional organelles. Damaged proteins that accumulate during stress can be refolded, ubiquitinated, and degraded by the proteasome pathway, or aggregated and degraded by autophagy. To direct damaged or unfolded proteins to the autophagy pathway, p62 binds to polyubiquitinated proteins, forming protein aggregates by oligomerization, and to Atg8/LC3 on the autophagosome membrane to target aggregates to autophagosomes for degradation. Protein aggregation may be a protective mechanism to limit cellular exposure to toxic proteins through sequestration, as well as an efficient packaging and delivery mechanism that collects and directs damaged proteins to autophagosomes. Thus, the inability to dispose of p62 aggregates through autophagy appears to be toxic to normal tissues.

The ATG6/Beclin1-Vps34-ATG8/LC3 complex regulates autophagosome formation. LC3 cleavage, lipidation, and membrane translocation are frequently utilized to monitor autophagy induction. The mechanism by which starvation and stress activate autophagy is controlled in part through the PI-3 kinase pathway via the protein kinase mTOR. Growth factor and nutrient availability promote mTOR activation that suppresses autophagy, whereas starvation and mTOR inactivation stimulate autophagy (Klionsky (2007), Nat Rev Mol Cell Biol 8, 931-937). While there are other mechanisms to regulate autophagy, mTOR provides a link between nutrient and growth factor availability, growth control, autophagy, and metabolism.

Autophagy plays an essential role in maintaining protein quality control, while defective autophagy is involved in the development of diseases including, but not limited to, cancer, neurodegenerative disorders, autoimmune disorders, cardiovascular disorders, metabolic disorders, hamartoma syndrome, genetic muscle disorders, and myopathies. Therefore, there exists a need for identification of inhibitors of the autophagy survival pathway in, for example, cancer cells. Such inhibitors of autophagy can be used in the prevention, palliation, and/or treatment of cancer.

SUMMARY OF THE INVENTION

Disclosed is a compound of formula III:

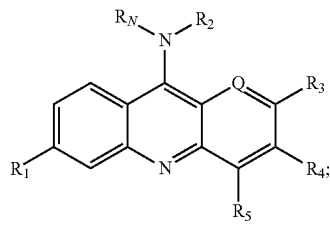

or a pharmaceutically acceptable salt thereof, wherein:
Q is CH or N;
$R_N$ is —H, $C_1$-$C_3$ alkyl, or —CO—$R_{N-1}$, where $R_{N-1}$ is $C_1$-$C_3$ alkyl or phenyl;
$R_1$ is —H, —F, —Cl, —Br, or —$CF_3$;
$R_2$ is —CH($R_{2-1}$)$_{n1}$—(CH$_2$)$_{n2}$—W$_{n3}$—X or —C*H—CH$_2$—CH$_2$—X$_2$—X$_3$—;
$n_1$ is 0 or 1;
$R_{2-1}$ is —H, $C_1$-$C_3$ alkyl, or $C_3$ cycloalkyl;
$n_2$ is 0 through 3;
$n_3$ is 0 or 1, with the provisos that (1) when $n_1$ or $n_2$ are other than 0, $n_3$ must be 0, (2) when $n_3$ is 1, $n_1$ and $n_2$ are both 0; (3) when $n_1$ is 1, $X_{1-2}$ and $X_{1-3}$ must be taken together with the attached nitrogen atom to form a monocyclic structure;
W is a cyclic structure of three through seven atoms consisting of carbon, nitrogen, and sulfur, with the proviso that there not be more than one nitrogen or sulfur atom in the ring optionally containing 1 through 3 double bonds;
X is —N$X_{1-2}X_{1-3}$, where $X_{1-2}$ and $X_{1-3}$ are the same or different and are $C_1$-$C_4$ substituted with one —OCH$_3$, —O—$C_2H_5$, alkoxy, haloalkoxy, haloalkyl, cyclopropyl, —CH$_2$-cyclopropyl, cyclobutyl, —SO$_2$—$X_{1-4}$ where $X_{1-4}$ is selected from —H and $C_1$-$C_3$ alkyl, —CO—$X_{1-4}$ where $X_{1-4}$ is as defined above, and where the $X_{1-2}$ and $X_{1-3}$ are taken together with the attached nitrogen atom to form a monocyclic structure consisting of four through seven atoms selected from the group consisting of carbon and nitrogen, with the proviso that the ring does not have more than two nitrogen atoms, —O—$X_{1-2}$ where $X_{1-2}$ is defined above;
$X_2$ is —N$X_{1-2}$— or —O—, where $X_{1-2}$ is defined above;
$X_3$ is —C*H—(CH$_2$)$_{n4}$— or —(CH$_2$)$_{n4}$—C*H— where $n_4$ is 0 through 2 and by convention * means the atoms marked with an asterisk (*) are bonded to each other resulting in the formation of a ring;
$R_3$ is —H, —F, —Cl, —Br, —$CF_3$, —$OR_{3-1}$ where $R_{3-1}$ is —H, $C_1$-$C_6$ alkyl or —CO—$R_{3-2}$ where $R_{3-2}$ is $C_1$-$C_3$ alkyl or phenyl, —N($R_{3-1}$)$_2$ where the $R_{3-1}$ are the same or different and are as defined above, —S$R_{3-1}$ where $R_{3-1}$ is as defined above, —S(O)—$R_{3-1}$ where $R_{3-1}$ is as defined above, or —SO$_2$—$R_{3-1}$ where $R_{3-1}$ is as defined above;
$R_4$ is —H, —F, —Cl, —Br, —$CF_3$, —$OR_{4-1}$ where $R_{4-1}$ is —H, $C_1$-$C_6$ alkyl or —CO—$R_{4-2}$ where $R_{4-2}$ is $C_1$-$C_3$ alkyl or phenyl, —N($R_{4-1}$)$_2$ where the $R_{4-1}$ are the same or different and are as defined above, —$S_{4-1}$ where $R_{4-1}$ is as defined above, —S(O)—$R_{4-1}$ where $R_{4-1}$ is as defined above, or —SO$_2$—$R_{4-1}$ where $R_{4-1}$ is as defined above;
$R_5$ is —H, —F, —Cl, —Br, —$CF_3$, —$OR_{5-1}$ where $R_{5-1}$ is —H, $C_1$-$C_6$ alkyl or —CO—$R_{5-2}$ where $R_{5-2}$ is $C_1$-$C_3$ alkyl or phenyl, —N($R_{5-1}$)$_2$ where the $R_{5-1}$ are the same or different and are as defined above, —S$R_{5-1}$ where $R_{5-1}$ is as defined above, —S(O)—$R_{5-1}$ where $R_{5-1}$ is as defined above, or —SO$_2$—$R_{5-1}$ where $R_{5-1}$ is as defined above;
with the proviso that one of $R_1$, $R_3$, $R_4$ and $R_5$ must be other than —H.

Also disclosed is a compound of formula V:

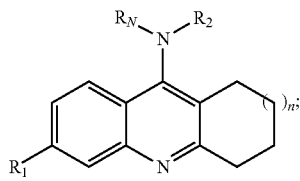

or a pharmaceutically acceptable salt thereof, wherein:
n is 0 or 1;
$R_2$ is —CH($R_{2-1}$)$_{n1}$—(CH$_2$)$_{n2}$—W$_{n3}$—X
$n_1$ is 0 or 1;
$R_{2-1}$ is —H or $C_1$-$C_3$ alkyl;
$n_2$ is 0 through 3;
$n_3$ is 0 or 1, with the provisos (1) that when $n_1$ or $n_2$ are other than 0, $n_3$ must be 0 and (2) that when $n_3$ is 1, $n_1$ and $n_2$ are both 0;
W is a cyclic structure of three through seven atoms consisting of carbon, nitrogen, and sulfur with the proviso that there not be more than one nitrogen or sulfur atom in the ring optionally containing 1 through 3 double bonds;
X is —N$X_{1-2}X_{1-3}$ or —C*H—CH$_2$—CH$_2$—X$_2$—X$_3$—;
$X_{1-2}$ and $X_{1-3}$ are the same or different and are —H, $C_1$-$C_4$ optionally substituted with one —OH, —OCH$_3$, —O—$C_2H_5$, cyclopropyl, —CH$_2$-cyclopropyl, cyclobutyl, —CH$_2$—CH$_2$—N($X_{1-4}$)($X_{1-5}$) where $X_{1-4}$ and $X_{1-5}$ are the same or different and are —H and $C_1$-$C_3$ alkyl, —SO$_2$—$X_{1-4}$ where $X_{1-4}$ is as defined above, —CO—$X_{1-4}$ where $X_{1-4}$ is as defined above, and where the $X_{1-2}$ and $X_{1-3}$ are taken together with the attached nitrogen atom to form a monocyclic structure consisting of four through seven atoms selected from the group consisting of carbon, nitrogen and oxygen with the provisos that the ring not have more than one oxygen atom and not more than two nitrogen atoms; —O—$X_{1-2}$ where $X_{1-2}$ is as defined above;
$X_2$ is —N$X_{1-2}$— or —O—,
$X_3$ is —CH—(CH$_2$)$_{m4}$— or —(CH$_2$)$_{m4}$—C*H— where $m_4$ is 0 through 2 and by convention * means the atoms marked with an asterisk (*) are bonded to each other resulting in the formation of a ring; and where $R_1$ and $R_N$ are defined above.

Also disclosed are pharmaceutical compositions containing compounds of formulas III or V.

Also disclosed are processes for preparing compounds of formulas III or V.

Also disclosed are methods of treating cancer, neurodegenerative disorders, autoimmune disorders, cardiovascular disorders, metabolic disorders, hamartoma syndrome, genetic muscle disorders, and myopathies, comprising administration to a patient in need of such treatment a compound of formula III or V or a pharmaceutically salt thereof.

DETAILED DESCRIPTION OF THE INVENTION

Abbreviations and Definitions

Figure 1:
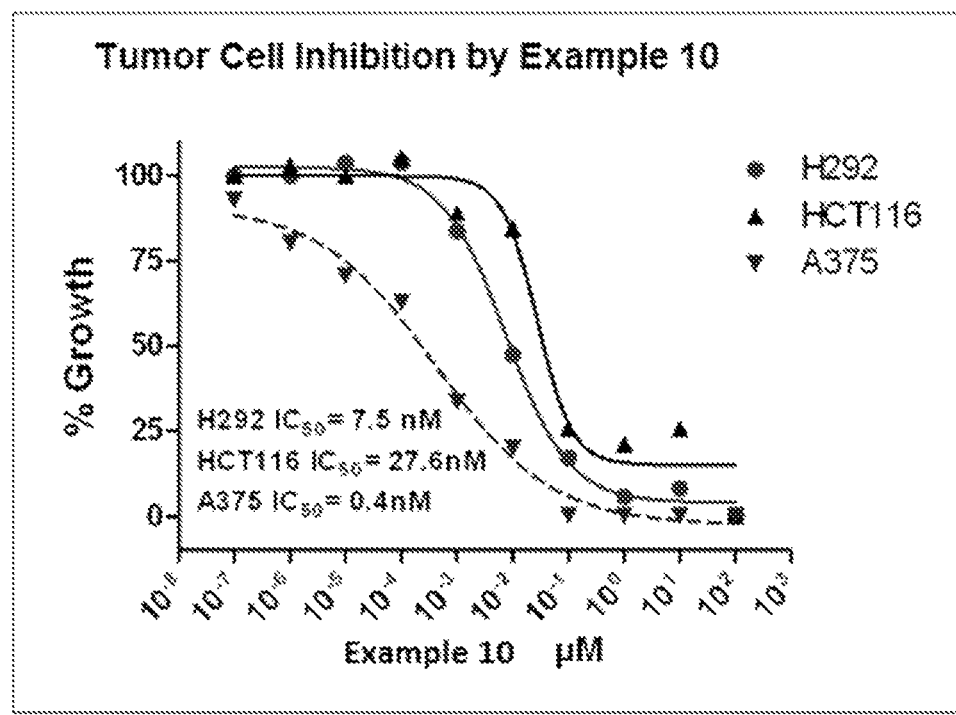
FIG. 1A depicts tumor cell inhibition by Example 10 in cell lines H292, HCT116, and A375.
FIG. 1B depicts tumor cell inhibition by Example 10 in cell lines HCC1569, A498, and N87.
Figure 1:
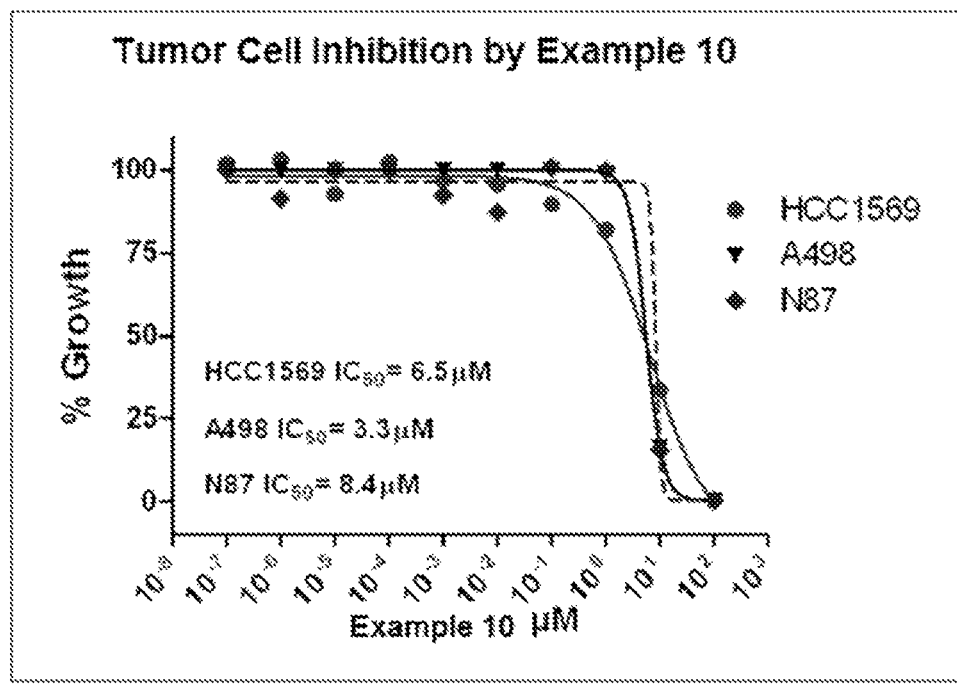
Figure 2:
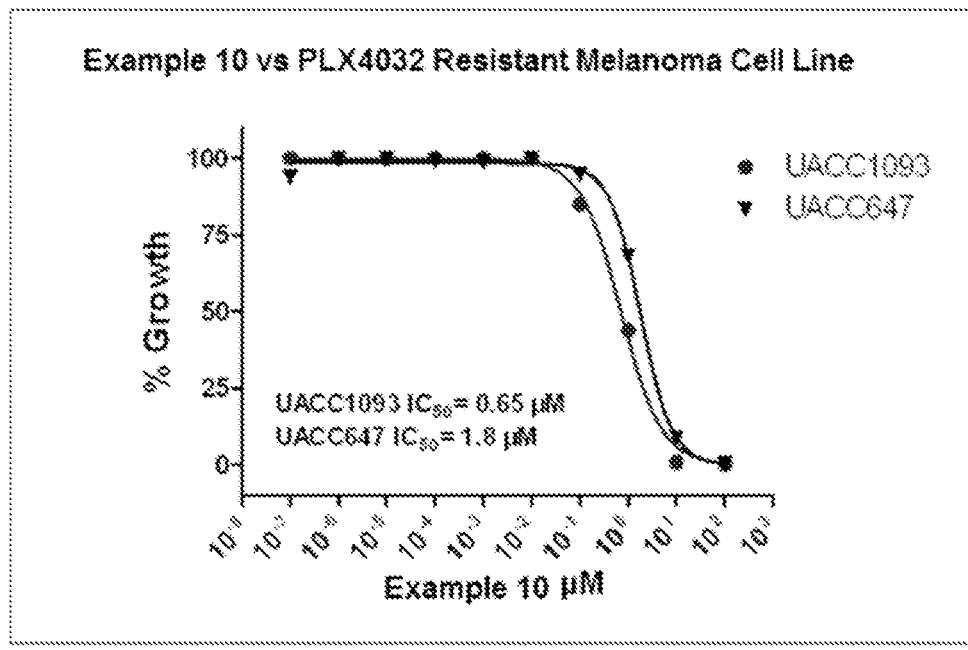
FIG. 2 depicts tumor cell inhibition by Example 10 in PLX-4032 resistant melanoma cell lines UACC1093 and UACC647.

The definitions and explanations below are for the terms as used throughout this entire document including both the specification and the claims.

| Abbreviation | Meaning |
| --- | --- |
| Ac | Acetyl |
| bALP | Bone-specific alkaline phosphatase |
| Br | Broad |
| °C. | Degrees Celsius |
| c- | Cyclo |
| CBZ | CarboBenZoxy = benzyloxycarbonyl |
| CTx | Cross-linked C-terminal telopeptides of type-1 collagen |
| d | Doublet |
| dd | Doublet of doublet |
| dt | Doublet of triplet |
| DCM | Dichloromethane |
| DME | 1,2-dimethoxyethane |
| DMF | N,N-Dimethylformamide |
| DMSO | dimethyl sulfoxide |
| g | Gram(s) |
| h or hr | Hour(s) |
| HPLC | High pressure liquid chromatography |
| L | Liter(s) |
| M | Molar or molarity |
| m | Multiplet |
| mg | Milligram(s) |
| MHz | Megahertz (frequency) |
| Min | Minute(s) |

| Abbreviation | Meaning |
| --- | --- |
| mL | Milliliter(s) |
| µL | Microliter(s) |
| µM | Micromole(s) or micromolar |
| mM | Millimolar |
| Mmol | Millimole(s) |
| Mol | Mole(s) |
| MS | Mass spectral analysis |
| N | Normal or normality |
| nM | Nanomolar |
| NMR | Nuclear magnetic resonance spectroscopy |
| q | Quartet |
| RT | Room temperature |
| s | Singlet |
| t or tr | Triplet |
| TFA | Trifluoroacetic acid |
| THF | Tetrahydrofuran |

The symbol "—" means a single bond, "=" means a double bond, "≡" means a triple bond. The symbol "⁓" refers to a group on a double-bond as occupying either position on the terminus of a double bond to which the symbol is attached; that is, the geometry, E- or Z-, of the double bond is ambiguous. When a group is depicted removed from its parent formula, the "~" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

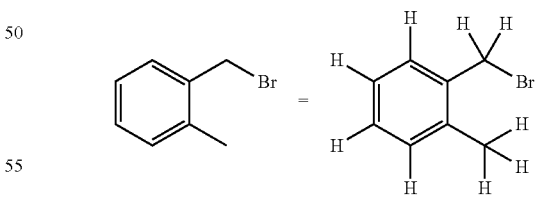

In this application, some ring structures are depicted generically and will be described textually. For example, in the schematic below, if in the structure on the left, ring A is used to describe a "spirocyclyl," then if ring A is cyclopropyl, there are at most four hydrogens on ring A (when "R" can also be —H). In another example, as depicted on the right side of the schematic below, if ring B is used to describe a "phenylene" then there can be at most four hydrogens on ring B (assuming depicted cleaved bonds are not C—H bonds).

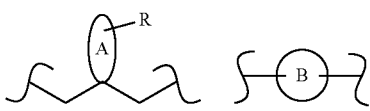

If a group "R" is depicted as "floating" on a ring system, as for example in the formula:

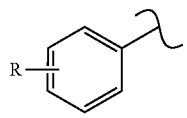

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

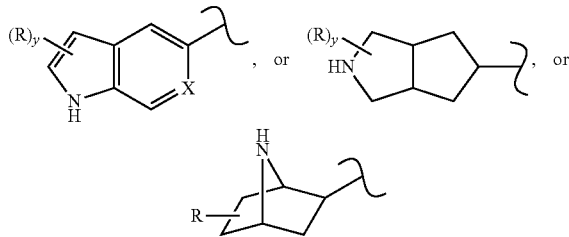

then, unless otherwise defined, a substituent "R" may reside on any atom of the fused ring system, assuming replacement of a depicted (for example the —NH— in the formula above), implied (for example as in the formula above, where the hydrogens are not shown but understood to be present), or expressly defined hydrogen (for example where in the formula above, "X" equals =CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When there are more than one such depicted "floating" groups, as for example in the formulae:

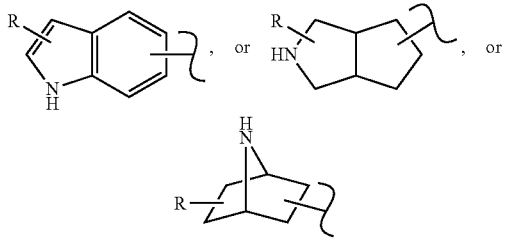

where there are two groups, namely, the "R" and the bond indicating attachment to a parent structure; then, unless otherwise defined, the "floating" groups may reside on any atoms of the ring system, again assuming each replaces a depicted, implied, or expressly defined hydrogen on the ring.

When a group "R" is depicted as existing on a ring system containing saturated carbons, as for example in the formula:

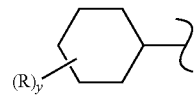

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

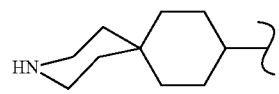

"Alkyl" is intended to include linear, branched, or cyclic hydrocarbon structures and combinations thereof, inclusively. For example, "$C_8$ alkyl" may refer to an n-octyl, iso-octyl, cyclohexylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more than eight carbon atoms. Exemplary alkyl groups are those of $C_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-yne radicals; and for example, "propyl" or "$C_3$ alkyl" each include n-propyl, propenyl, and isopropyl.

"Alkylene" refers to straight or branched chain divalent radical consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH(C_6H_{13})$).

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Amino" refers to the group —NH₂. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, furanyl-oxy-sulfonamino.

Aryl" refers to aromatic six- to fourteen-membered carbocyclic ring, for example, benzene, naphthalene, indane, tetralin, fluorene and the like, univalent radicals. As univalent radicals, the aforementioned ring examples are named, phenyl, naphthyl, indanyl, tetralinyl, and fluorenyl.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fined-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl radicals that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroatom" refers to O, S, N, or P.

"Heterocyclyl" refers to a stable three- to fifteen-membered ring radical that consists of carbon atoms and from one to five heteroatoms selected from the group consisting of nitrogen, phosphorus, oxygen and sulfur. For purposes of this invention, the heterocyclyl radical may be a monocyclic, bicyclic or tricyclic ring system, which may include fused or bridged ring systems as well as spirocyclic systems; and the nitrogen, phosphorus, carbon or sulfur atoms in the heterocyclyl radical may be optionally oxidized to various oxidation states. In a specific example, the group —S(O)0-2-, refers to —S— (sulfide), —S(O)— (sulfoxide), and —SO2- (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring radical may be partially or fully saturated or aromatic. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl radical. A heteroalicyclic may contain unsaturation, but is not aromatic.

"Heteroaryl" refers specifically to an aromatic heterocyclyl radical.

"Heterocyclylalkyl" refers to a residue in which a heterocyclyl is attached to a parent structure via one of an alkylene, alkylidene, or alkylidyne radical. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl, and the corresponding alkylene, alkylidene, or alkylidyne radical portion of a heterocyclylalkyl group may be optionally substituted. "Lower heterocyclylalkyl" refers to a heterocyclylalkyl where the "alkyl" portion of the group has one to six carbons. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic Such terms may be described in more than one way, for example, "lower heterocyclylalkyl" and "heterocyclyl C1-6alkyl" are equivalent terms.

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, that only sterically practical and/or synthetically feasible compounds are meant to be included. "Optionally substituted" refers to all subsequent modifiers in a term, for example in the term "optionally substituted arylC1-8 alkyl," optional substitution may occur on both the "C1-8 alkyl" portion and the "aryl" portion of the molecule; and for example, optionally substituted alkyl includes optionally substituted cycloalkyl groups, which in turn are defined as including optionally substituted alkyl groups, potentially ad infinitum. A list of exemplary optional substitution are listed below in the definition of "substituted."

"Substituted" alkyl, aryl, and heterocyclyl, refer respectively to alkyl, aryl, and heterocyclyl, wherein one or more (for example up to about five, in another example, up to about three) hydrogen atoms are replaced by a substituent independently selected from: optionally substituted alkyl (for example, fluoromethyl), optionally substituted aryl (for example, 4-hydroxyphenyl), optionally substituted arylalkyl (for example, 1-phenyl-ethyl), optionally substituted heterocyclylalkyl (for example, 1-pyridin-3-yl-ethyl), optionally substituted heterocyclyl (for example, 5-chloro-pyridin-3-yl or 1-methyl-piperidin-4-yl), optionally substituted alkoxy, alkylenedioxy (for example methylenedioxy), optionally substituted amino (for example, alkylamino and dialkylamino), optionally substituted amidino, optionally substituted aryloxy (for example, phenoxy), optionally substituted arylalkyloxy (for example, benzyloxy), carboxy (—CO2H), carboalkoxy (that is, acyloxy or —OC(=O)R), carboxyalkyl (that is, esters or —CO2R), carboxamido, benzyloxycarbonylamino (CBZ-amino), cyano, acyl, halogen, hydroxy, nitro, sulfanyl, sulfinyl, sulfonyl, thiol, halogen, hydroxy, oxo, carbamyl, acylamino, and sulfonamido.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —S(O2)-H, —S(O2)-(optionally substituted alkyl), —S(O2)-optionally substituted aryl), —S(O2)-(optionally substituted heterocyclyl), —S(O2)-(optionally substituted alkoxy), —S(O2)-optionally substituted aryloxy), and —S(O2)-(optionally substituted heterocyclyloxy).

"Yield" for each of the reactions described herein is expressed as a percentage of the theoretical yield.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent radical, for example, —OCH2-, then it is understood that either of the two partners may be bound to the particular group at one end, and the other partner is necessarily bound to the other end of the particular group, unless stated explicitly otherwise. Stated another way, divalent radicals are not to be construed as limited to the depicted orientation, for example "—OCH2-" is meant to mean not only "—OCH2-" as drawn, but also "—CH2O—."

With regard to various cyclic substituents, such as those within the scope of group W such as pyridinyl, when various positions of attachment are possible, such as for pyridine (i.e., pyridin-2-yl, pyridin-3-yl, and pyridin-4-yl), all are within the scope of the present invention.

Methods for the preparation and/or separation and isolation of single stereoisomers from racemic mixtures or nonracemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as 2H and 3H, carbon, such as 11C, 13C and 14C, chlorine, such as 36Cl, fluorine, such as 18F, iodine, such as 123I and 125I, nitrogen, such as 13N and 15N, oxygen, such as 15O, 17O and 18O, phosphorus, such as 32P, and sulphur, such as 35S. Certain isotopically-labelled compounds of formula (I), for example, those incorporating a radioactive isotope, are useful in drug and/or substrate tissue distribution studies. The radioactive isotopes tritium, i.e. 3H, and carbon-14, i.e. 14C, are particularly useful for this purpose in view of their ease of incorporation and ready means of detection. Substitution with heavier isotopes such as deuterium, i.e. 2H, may afford certain therapeutic advantages resulting from greater metabolic stability, for example, increased in vivo half-life or reduced dosage requirements, and hence may be preferred in some circumstances. Substitution with positron emitting isotopes, such as 11C, 18F, 15O and 13N, can be useful in Positron Emission Topography (PET) studies for examining substrate receptor occupancy. Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

"Patient" for the purposes of the present invention includes humans and other animals, particularly mammals, and other organisms. Thus the methods are applicable to both human therapy and veterinary applications. More specifically, the patient is a mammal, and in some embodiments, the patient is human.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his/her own knowledge and to this disclosure.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treatment" or a "treating" a condition as used herein is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease.

"Treating" or "treatment" as used herein includes the treatment of a cancer in a human, which cancer is characterized by abnormal cellular proliferation, and invasion and includes at least one of (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

All temperatures are in degrees Celsius (° C.). 20-25° C. denotes room temperature.

Chromatography (column and flash chromatography) refers to purification/separation of compounds expressed as (support, eluent). It is understood that the appropriate fractions are pooled and concentrated to give the desired compound(s).

Saline refers to an aqueous saturated sodium chloride solution.

Alcohol refers to ethyl alcohol.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance, and bioavailability.

When solvent pairs are used, the ratios of solvents used are volume/volume (v/v).

When the solubility of a solid in a solvent is used the ratio of the solid to the solvent is weight/volume (wt/v).

The invention further encompasses aspects in which a protecting group is added to the compound. One skilled in the art would recognize that during the synthesis of complex molecules, one group on the disclosed compound may happen to interfere with an intended reaction that includes a second group on the compound. Temporarily masking or protecting the first group encourages the desired reaction. Protection involves introducing a protecting group to a group to be protected, carrying out the desired reaction, and removing the protecting group. Removal of the protecting group may be referred to as deprotection. Examples of compounds to be protected in some syntheses include hydroxy groups, amine groups, carbonyl groups, carboxyl groups, and thiols.

A protecting group may result from any chemical synthesis that selectively attaches a group that is resistant to certain reagents to the chemical group to be protected without significant effects on any other chemical groups in the molecule, remains stable throughout the synthesis, and is removed through conditions that do not adversely react with the protected group, nor any other chemical group in the molecule.

Protecting groups, reagents that add those groups, preparations of those reagents, protection and deprotection strategies under a variety of conditions, including complex syntheses with mutually complementary protecting groups, are all well known in the art. Examples of all of these may be found in Green et al, Protective Groups in Organic Chemistry 2nd Ed., (Wiley 1991), and Harrison et al, Compendium of Synthetic Organic Methods, Vols. 1-8 (Wiley, 1971-1996) both of which hereby incorporated by reference in its entirety.

Racemates, individual enantiomers, or diasteromers of the disclosed compound are prepared by specific synthesis or resolution through known methods. For example, the disclosed compound may be resolved into it enantiomers by the formation of diasteromeric pairs through salt formation using an optically active acid. Enantiomers are fractionally crystallized and the free base regenerated. In another example, enantiomers may be separated by chromatography. Such chromatography is any appropriate method that is appropriate to separate enantiomers such as HPLC on a chiral column as is known to those skilled in the art.

Cancer cells include any cells derived from a tumor, neoplasm, cancer, precancer, cell line, or any other source of cells that are ultimately capable of potentially unlimited expansion and growth. Cancer cells may be derived from naturally occurring sources or may be artificially created. Cancer cells may also be capable of invasion into other tissues and metastasis when placed into an animal host. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Expansion of a cancer cell includes any process that results in an increase in the number of individual cells derived from a cancer cell. Expansion of a cancer cell may result from mitotic division, proliferation, or any other form of expansion of a cancer cell, whether in vitro or in vivo. Expansion of a cancer cell further encompasses invasion and metastasis. A cancer cell may be in physical proximity to cancer cells from the same clone or from different clones that may or may not be genetically identical to it. Such aggregations may take the form of a colony, tumor or metastasis, any of which may occur in vivo or in vitro. Slowing the expansion of the cancer cell may be brought about either by inhibiting cellular processes that promote expansion or by bringing about cellular processes that inhibit expansion. Processes that inhibit expansion include processes that slow mitotic division and processes that promote cell senescence or cell death. Examples of specific processes that inhibit expansion include capsase dependent and independent pathways, autophagy, necrosis, apoptosis, and mitochondrial dependent and independent processes.

Treatment is contemplated in living entities including but not limited to mammals (particularly humans) as well as other mammals include livestock (horses, cattle, sheep, pigs) and other animals generally bred for domesticated companion animals such as dogs and cats.

Compounds

As indicated previously, in one aspect, the invention is directed to a compound of formula III

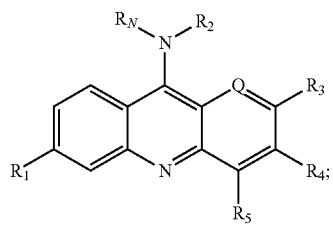

or a pharmaceutically acceptable salt thereof.

In some embodiments of a compound of formula III, Q is CH.

In some embodiments, $R_1$ is —F, —Cl, or —Br. More particularly, $R_1$ is —Cl.

In some embodiments, $R_3$ is —$OR_{34}$. More particularly, $R_{3-1}$ is —Cl.

In some embodiments, $R_4$ and $R_5$ are —H.

In some embodiments RN is —H.

When $X_{1-2}$ and $X_{1-3}$ are taken together with the attached nitrogen atom to form a monocyclic structure consisting of four through seven atoms selected from the group consisting of carbon and nitrogen, the cyclic structure can be either saturated like piperazinyl or aromatic like pyridinyl.

Thus, in some embodiments, the monocyclic structure be selected from the group consisting of piperazin-1-yl optionally substituted in the 4-position with C1-C3 alkyl, —CO— ($C_1$-$C_3$ alkyl), —$SO_2$—H, or —$SO_2$—($C_1$-$C_3$) alkyl; piperidin-1-yl and piperidin-4-yl both optionally substituted with one —F, —Cl, $C_1$-$C_3$ alkyl, —CO—($C_1$-$C_3$ alkyl), —$SO_2$—H, or —$SO_2$—(C1-C3) alkyl; and pyrrolidin-1-yl, pyrrolinin-2-yl, and pyrrolidin-3-yl all optionally substituted with one —F, —Cl, C1-$C_3$ alkyl, —CO—($C_1$-$C_3$ alkyl), —$SO_2$—H, or —SO2-($C_1$-$C_3$) alkyl.

More particularly, $X_{1-2}$ and $X_{1-3}$ are cyclized to form pyrrolidin-1-yl, N-(1-methylpyrrolidin-3-yl), N-(4-methylpiperazin-1-yl), and N-(1-ethylpiperadin-4-yl).

Also, when W is a cyclic structure of three through seven atoms consisting of carbon, nitrogen, and sulfur, the cyclic structure be selected from the group consisting of phenyl, thiazolyl, pyridinyl, and $C_3$-$C_7$ cycloalkyl.

In some embodiments, the compound of formula III is a compound selected from Examples 5, 7, 10, and 16.

One embodiment of a compound of formula III is a compound of formula III(a):

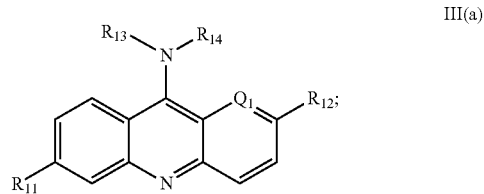

or a pharmaceutically acceptable salt thereof, wherein:
$Q_1$ is selected from the group consisting of CH and N;
$R_{11}$ is selected from the group consisting of H, F, Cl, Br, and $C_{1-3}$ haloalkyl;
$R_{12}$ is selected from the group consisting of H, F, Cl, Br, OH, $C_{1-3}$ alkyl, $C_{1-3}$ haloalkyl, and $C_{1-3}$ alkoxy;
$R_{13}$ is selected from the group consisting of H, $C_{1-3}$ alkyl, and $C_{1-3}$ haloalkyl;
$R_{14}$ is selected from the group consisting of optionally substituted 5- or 6-membered cycloalkyl or heterocycloalkyl, optionally substituted

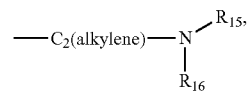

optionally substituted

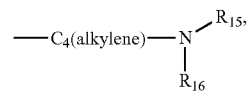

and optionally substituted

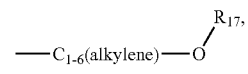

wherein the alkylene chains may be optionally substituted with up to 3 $R_{18}$;
$R_{15}$ and $R_{16}$ are each independently selected from the group consisting of H, alkyl, cycloalkyl, alkoxy, alkylamino, and sulfonyl;

or $R_{15}$ and $R_{16}$ may be joined together to form an optionally substituted 5- or 6-membered cycloalkyl or heterocycloalkyl;

$R_{17}$ is selected from the group consisting of H, alkyl, cycloalkyl, alkoxy, alkylamino, and sulfonyl; and $R_{18}$ is selected from the group consisting of H, alkyl, cycloalkyl, alkoxy, alkylamino, and sulfonyl.

In one embodiment of the compound of formula III(a), $Q_1$ is CH.

In another embodiment, $Q_1$ is N.
In one embodiment, $R_{11}$ is H, F, or Cl.
More particularly, $R_{11}$ is H.
In another embodiment, $R_{11}$ is F.
In yet another embodiment, $R_{11}$ is Cl.
In one embodiment, $R_{12}$ is H, F, Cl, OH, or $C_{1-3}$ alkoxy;
More particularly, $R_{12}$ is F or $C_{1-3}$ alkoxy.
More particularly, $R_{12}$ is F.
In another embodiment, $R_{12}$ is $C_{1-3}$ alkoxy.
More particularly, $R_{12}$ is methoxy.
In one embodiment, $R_{13}$ is H.
In another embodiment, $R_{13}$ is $C_{1-3}$ alkyl.
More particularly, $R_{13}$ is methyl.
In one embodiment, $R_{11}$ is $C_1$, and $R_{12}$ is methoxy.
In another embodiment, $Q_1$ is N, and $R_{12}$ is methoxy.
In another embodiment, $Q_1$ is N, and $R_{12}$ is H.
In another embodiment, $R_{11}$ is Br, and $R_{12}$ is methoxy.
In another embodiment, $R_{11}$ is F, and $R_{12}$ is methoxy.
In another embodiment, $Q_1$ is CH, and $R_{12}$ is Cl or F.
In one embodiment, $R_{13}$ is H, and $Q_1$ is CH.
In another embodiment, $R_{11}$ is Cl, and $R_{13}$ is H.

In any of the above embodiments of a compound of formula III(a) provided above, $R_{14}$ is an optionally substituted 5- or 6-membered cycloalkyl or heterocycloalkyl,

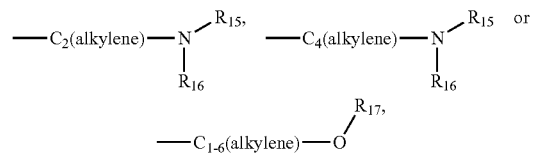

wherein the alkylene chains may be optionally substituted with up to 3 $R_{18}$.

In some embodiments, $R_{14}$ is an optionally substituted 5- or 6-membered heterocycloalkyl.

More particularly, $R_{14}$ is

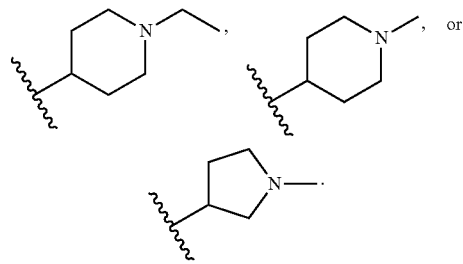

In some embodiments, $R_{14}$ is optionally substituted

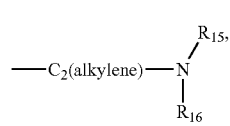

wherein the alkylene chain may be optionally substituted with up to 3 $R_{18}$.

More particularly, $R_{14}$ is

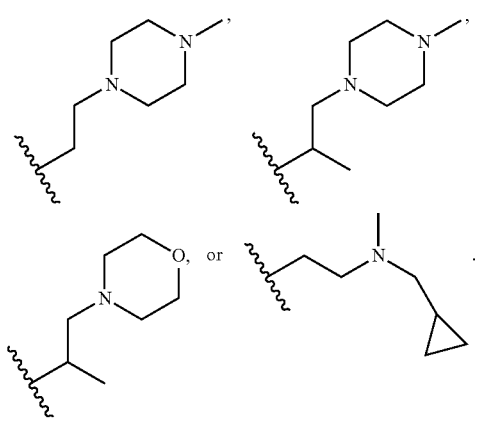

In some embodiments, $R_{14}$ is optionally substituted

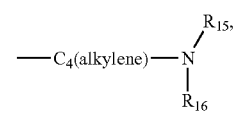

wherein the alkylene chain may be optionally substituted with up to 3 $R_{18}$.

More particularly, in some embodiments, $R_{14}$ is

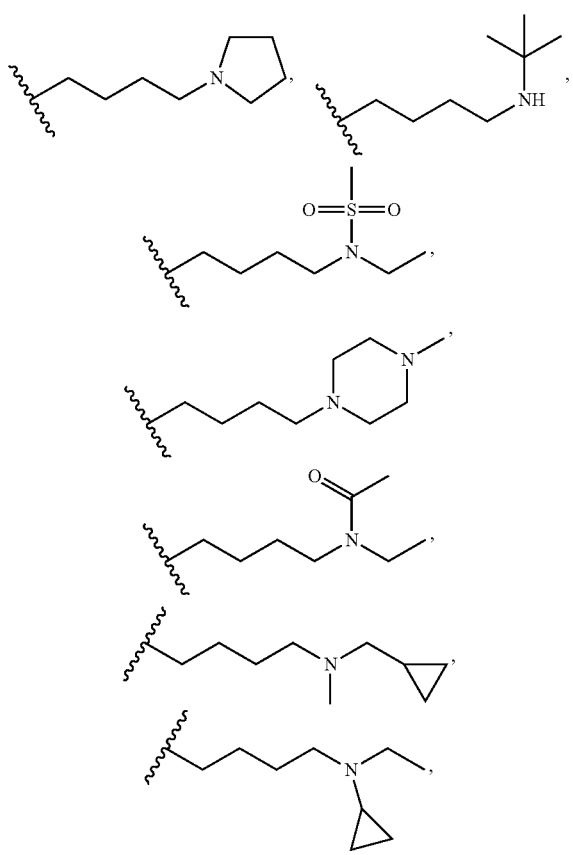

-continued

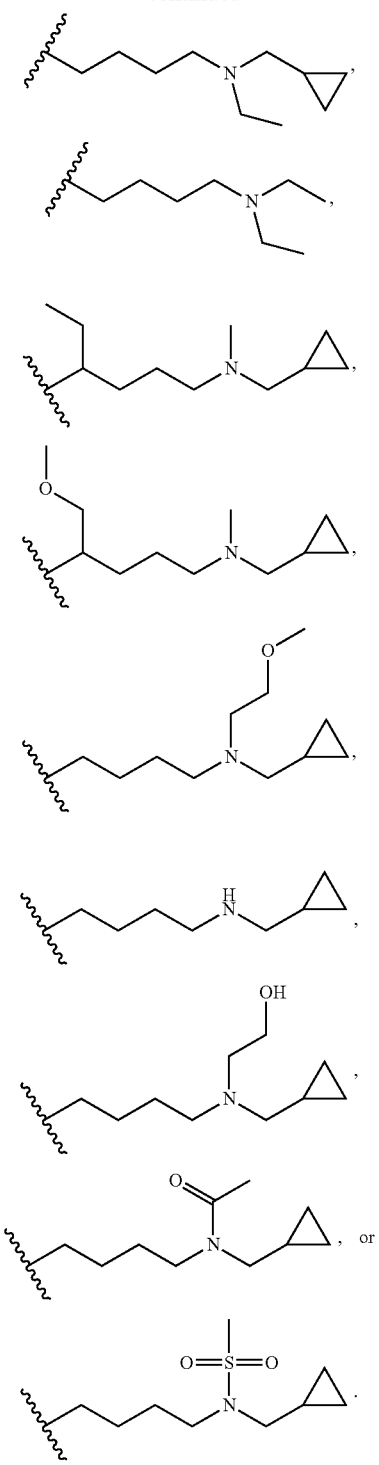

In some embodiments, $R_{14}$ is optionally substituted

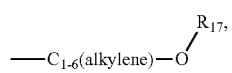

wherein the alkylene chain may be optionally substituted with up to 3 $R_{18}$.

More particularly, $R_{14}$ is

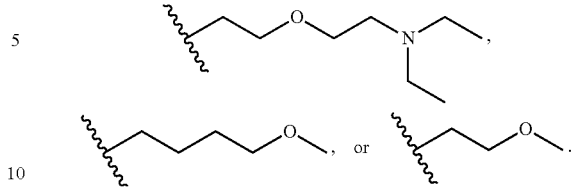

In another aspect, the invention is directed to a compound of formula V

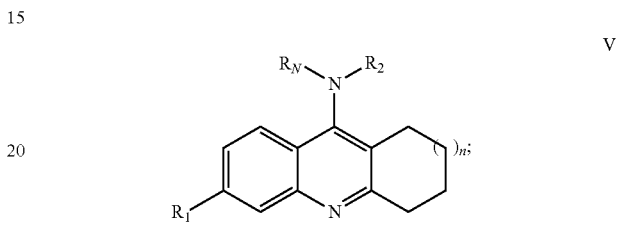

or a pharmaceutically acceptable salt thereof.

In some embodiments, $R_1$ is —F, —Cl, and —Br. More particularly, $R_1$ is —Cl.

In some embodiments, $R_N$ is —H. In some embodiments, $X_{1-2}$ and $X_{1-3}$ are taken together with the attached nitrogen atom to form a monocyclic structure consisting of four through seven atoms selected from the group consisting of carbon, nitrogen and oxygen. In some embodiments, the monocyclic structure be selected from the group consisting of where $X_{1-2}$ and $X_{1-3}$ are cyclized to form a cyclic structure selected from the group consisting of piperazin-1-yl optionally substituted in the 4-position with $C_1$-$C_3$ alkyl, —CO—($C_1$-$C_3$ alkyl), —$SO_2$—H, or —$SO_2$—($C_1$-$C_3$) alkyl; piperidin-1-yl and piperidin-4-yl both optionally substituted with one —F, —Cl, $C_1$-$C_3$ alkyl, —CO—($C_1$-$C_3$ alkyl), —$SO_2$—H, or —$SO_2$—($C_1$-$C_3$) alkyl; morpholin-1-yl optionally substituted with one —F, —Cl, $C_1$-$C_3$ alkyl, —CO—($C_1$-$C_3$ alkyl), —$SO_2$—H, or —$SO_2$—($C_1$-$C_3$) alkyl; pyrrolidin-1-yl, pyrrolinin-2-yl, and pyrrolidin-3-yl all optionally substituted with one —F, —Cl, $C_1$-$C_3$ alkyl, —CO—($C_1$-$C_3$ alkyl), —$SO_2$—H, or —$SO_2$—($C_1$-$C_3$).

More particularly, $X_{1-2}$ and $X_{1-3}$ are cyclized to form pyrrolidin-1-yl, N-(1-methylpyrrolidin-3-yl), N-(4-methylpiperazin-1-yl), and N-(1 ethylpiperadin-4-yl).

Also, when W is a cyclic structure of three through seven atoms consisting of carbon, nitrogen, and sulfur, that the cyclic structure be selected from the group consisting of phenyl, thiazolyl, pyridinyl, and $C_3$-$C_7$ cycloalkyl.

One embodiment of a compound of formula V is a compound of formula V(a):

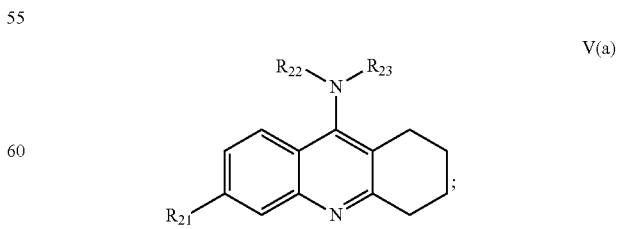

or a pharmaceutically acceptable salt thereof, wherein:
$R_{21}$ is selected from the group consisting of H, F, Cl, Br, and $C_{1-3}$ haloalkyl;

$R_{22}$ is selected from the group consisting of H, $C_{1-3}$ alkyl, and $C_{1-3}$ haloalkyl;

$R_{23}$ is selected from the group consisting of an optionally substituted 5- or 6-membered cycloalkyl or heterocycloalkyl, optionally substituted

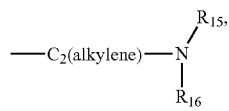

optionally substituted

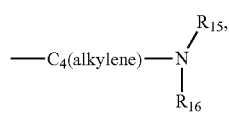

and optionally substituted

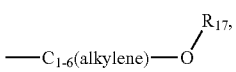

wherein the alkylene chains may be optionally substituted with up to 3 $R_{18}$;

$R_{15}$ and $R_{16}$ are each independently selected from the group consisting of H, alkyl, cycloalkyl, alkoxy, alkylamino, and sulfonyl;

or $R_{15}$ and $R_{16}$ may be joined together to form an optionally substituted 5- or 6-membered cycloalkyl or heterocycloalkyl;

$R_{17}$ is selected from the group consisting of H, alkyl, cycloalkyl, alkoxy, alkylamino, and sulfonyl; and $R_{18}$ is selected from the group consisting of H, alkyl, cycloalkyl, alkoxy, alkylamino, and sulfonyl.

In one embodiment, $R_{21}$ is H, F, or Cl.
More particularly, $R_{21}$ is H.
In another embodiment, $R_{21}$ is F.
In yet another embodiment, $R_{21}$ is Cl.
In one embodiment, $R_{22}$ is H.
In another embodiment, $R_{22}$ is $C_{1-3}$ alkyl.
More particularly, $R_{22}$ is methyl.
In one embodiment, $R_{21}$ is Cl, and $R_{22}$ is H
In another embodiment, $R_{21}$ is Br, and $R_{22}$ is H.
In another embodiment, $R_{21}$ is F, and $R_{22}$ is methyl.

In any of the above embodiments of a compound of formula III(a) provided above, $R_{22}$ is an optionally substituted 5- or 6-membered cycloalkyl or heterocycloalkyl,

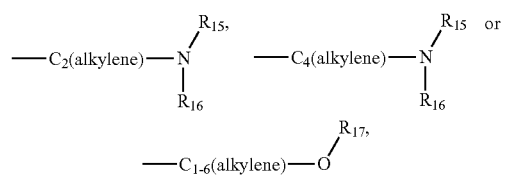

wherein the alkylene chains may be optionally substituted with up to 3 $R_{18}$.

In some embodiments, $R_{22}$ is optionally substituted 5- or 6-membered heterocycloalkyl.

More particularly, $R_{22}$ is

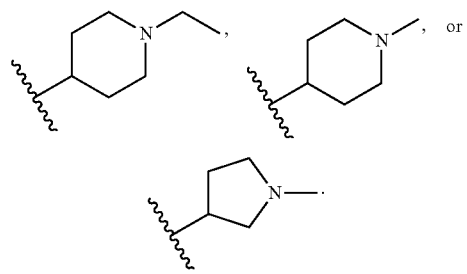

In some embodiments, $R_{22}$ is optionally substituted

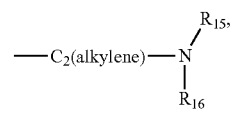

wherein the alkylene chain may be optionally substituted with up to 3 $R_{18}$.

More particularly, $R_{22}$ is

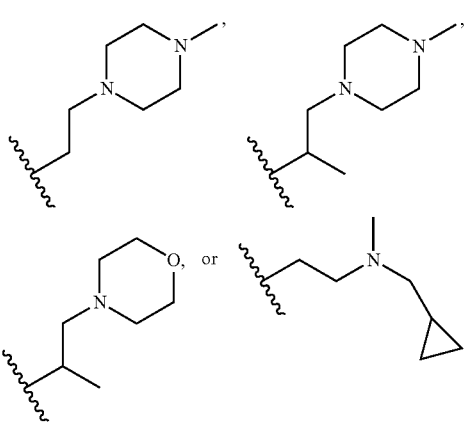

In some embodiments, $R_{22}$ is optionally substituted

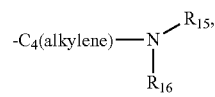

wherein the alkylene chain may be optionally substituted with up to 3 $R_{18}$.

More particularly, in some embodiments, $R_{22}$ is

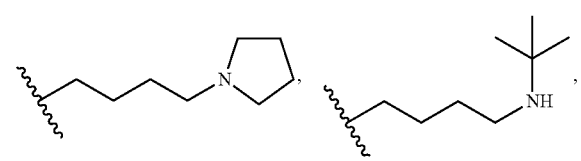

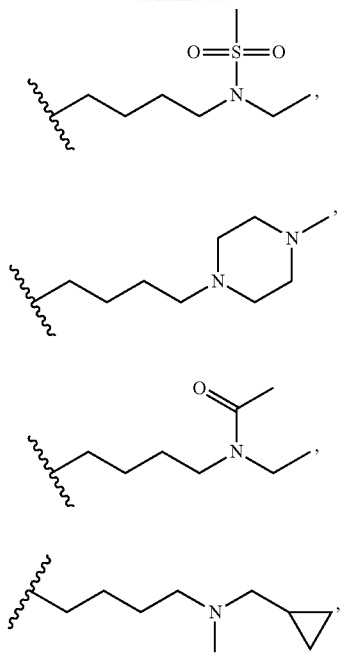

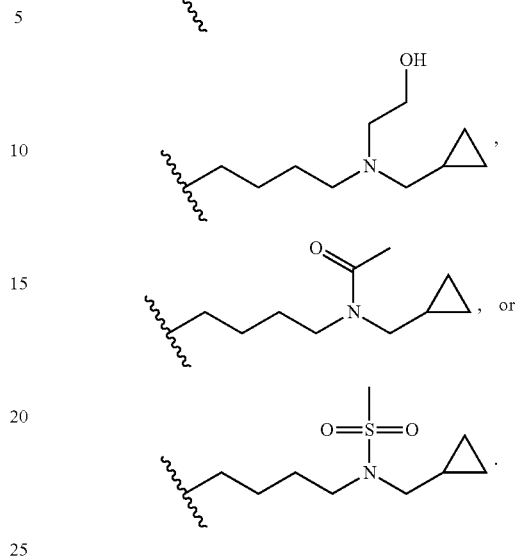

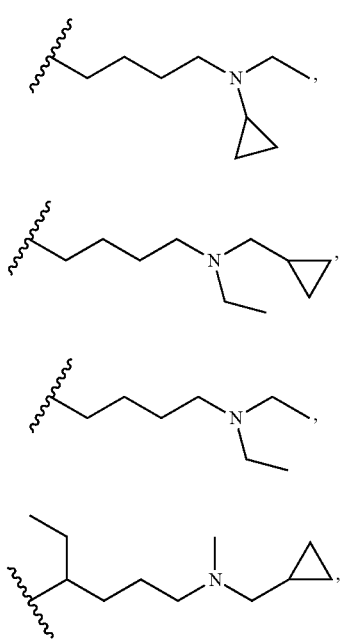

In some embodiments, $R_{22}$ is optionally substituted $$-C_{1\text{-}6}(\text{alkylene})-O^{R_{17}},$$

wherein the alkylene chain may be optionally substituted with up to 3 $R_{18}$.

More particularly, $R_{22}$ is

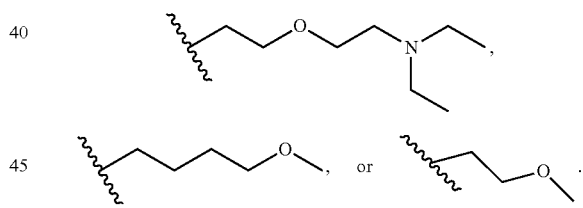

In another embodiment of a compound of formula V, the compounds are of formula V(b)

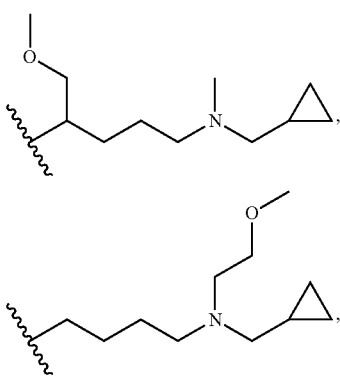

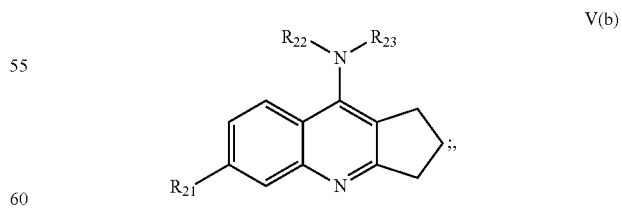

or a pharmaceutically acceptable salt thereof, wherein the variables and embodiments are as defined above for a compound of formula V(a).

In one aspect, the compound of the invention is selected from the compounds provided in Table 1:

TABLE 1

| Example | Structure | Name |
|---|---|---|
| 1 | 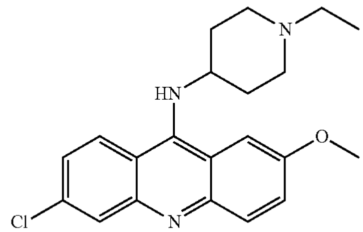 [SMILES: CCN1CCC(Nc2c3ccc(Cl)cc3nc3ccc(OC)cc23)CC1] | 6-Chloro-N-(1-ethylpiperidin-4-yl)-2-methoxyacridin-9-amine |
| 2 | 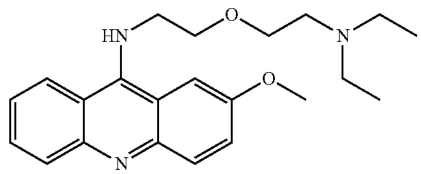 [SMILES: CCN(CC)CCOCCNc1c2ccccc2nc2ccc(OC)cc12] | 6-Chloro-N-(2-(2-(diethylamino)ethoxy)ethyl)-2-methoxyacridin-9-amine |
| 3 | 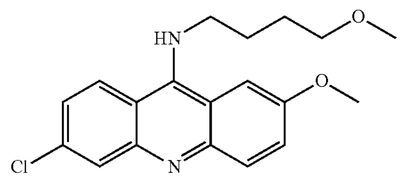 [SMILES: COCCCCNc1c2ccc(Cl)cc2nc2ccc(OC)cc12] | 6-Chloro-2-methoxy-N-(4-methoxybutyl)acridin-9-amine |
| 4 | 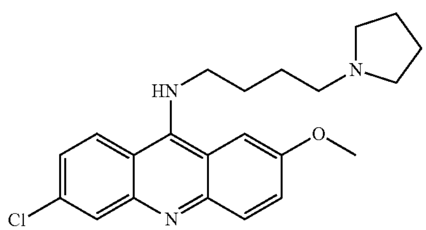 [SMILES: COc1ccc2nc3cc(Cl)ccc3c(NCCCCN3CCCC3)c2c1] | 6-Chloro-2-methoxy-N-(4-(pyrrolidin-1-yl)butyl)acridin-9-amine |
| 5 | 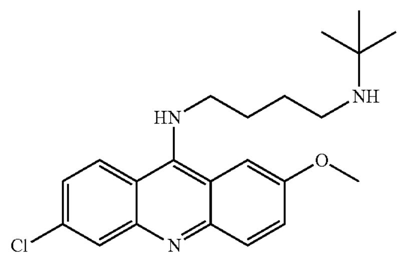 [SMILES: COc1ccc2nc3cc(Cl)ccc3c(NCCCCNC(C)(C)C)c2c1] | $N^1$-tert-butyl-$N^4$-(6-chloro-2-methoxyacridin-9-yl)butane-1,4-diamine |
| 6 | 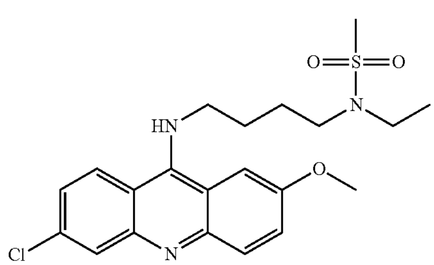 [SMILES: CCN(CCCCNc1c2ccc(Cl)cc2nc2ccc(OC)cc12)S(C)(=O)=O] | N-(4-(6-Chloro-2-methoxyacridin-9-ylamino)butyl)-N-ethylmethanesulfonamide |
| 7 | 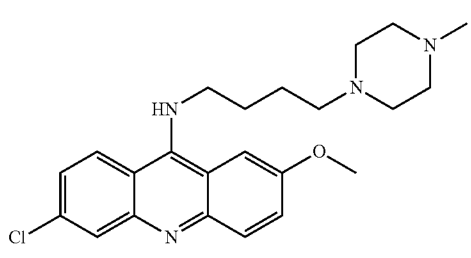 [SMILES: COc1ccc2nc3cc(Cl)ccc3c(NCCCCN3CCN(C)CC3)c2c1] | 6-Chloro-2-methoxy-N-(4-(4-methylpiperazin-1-yl)butyl)acridin-9-amine |

TABLE 1-continued

| Example | Structure | Name |
|---|---|---|
| 8 | 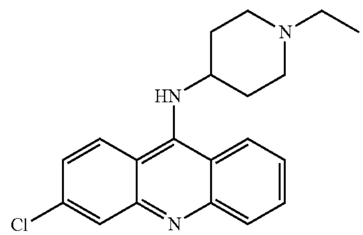 [SMILES: CCN1CCC(Nc2c3ccccc3nc3cc(Cl)ccc23)CC1] | 3-Chloro-N-(1-ethylpiperidin-4-yl)acridin-9-amine |
| 9 | 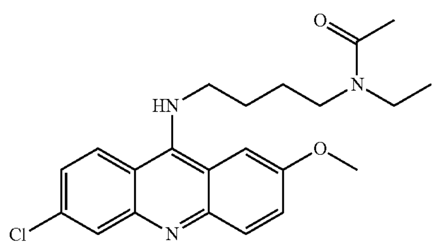 [SMILES: CCN(CCCCNc1c2ccc(Cl)cc2nc2ccc(OC)cc12)C(C)=O] | N-(4-(6-Chloro-2-methoxyacridin-9-ylamino)butyl)-N-ethylacetamide |
| 10 | 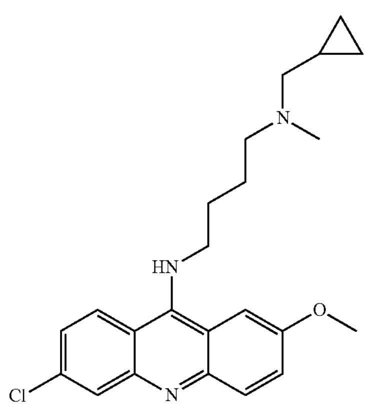 [SMILES: COc1ccc2nc3cc(Cl)ccc3c(NCCCCN(C)CC3CC3)c2c1] | $N^1$-(6-Chloro-2-methoxyacridin-9-yl)-$N^4$-(cyclopropylmethyl)-$N^4$-methylbutane-1,4-diamine |
| 11 | 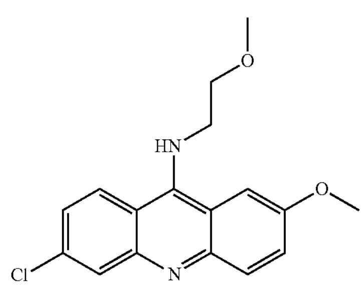 [SMILES: COCCNc1c2ccc(Cl)cc2nc2ccc(OC)cc12] | 6-Chloro-2-methoxy-N-(2-methoxyethyl)acridin-9-amine |
| 12 | 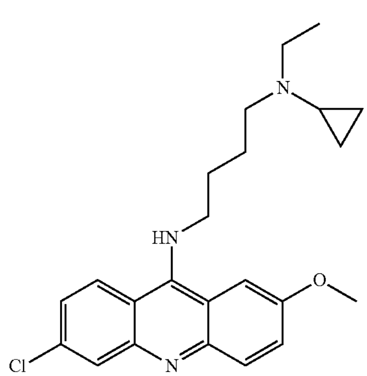 [SMILES: CCN(CCCCNc1c2ccc(Cl)cc2nc2ccc(OC)cc12)C1CC1] | $N^1$-(6-Chloro-2-methoxyacridin-9-yl)-$N^4$-cyclopropyl-$N^4$-ethylbutane-1,4-diamine |

TABLE 1-continued

| Example | Structure | Name |
|---|---|---|
| 13 | 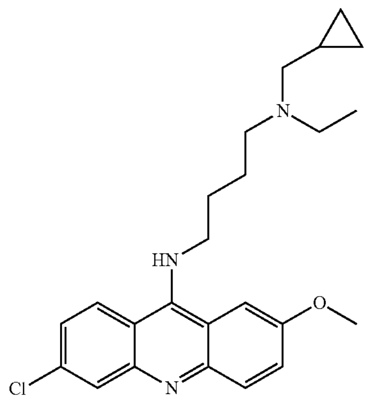 [SMILES: CCN(CCCCNc1c2ccc(Cl)cc2nc2ccc(OC)cc12)CC1CC1] | $N^1$-(6-Chloro-2-methoxyacridin-9-yl)-$N^4$-(cyclopropylmethyl)-$N^4$-ethylbutane-1,4-diamine |
| 14 | 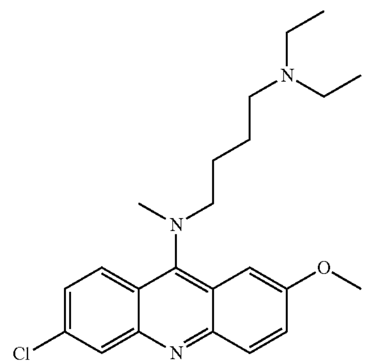 [SMILES: CCN(CC)CCCCN(C)c1c2ccc(Cl)cc2nc2ccc(OC)cc12] | $N^1$-(6-Chloro-2-methoxyacridin-9-yl)-$N^4$,$N^4$-diethyl-$N^1$-methylbutane-1,4-diamine |
| 15 | 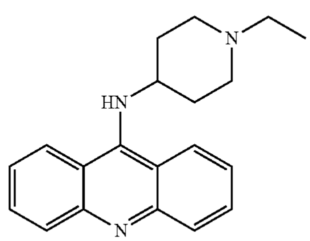 [SMILES: CCN1CCC(Nc2c3ccccc3nc3ccccc23)CC1] | N-(1-Ethylpiperidin-4-yl)acridin-9-amine |
| 16 | 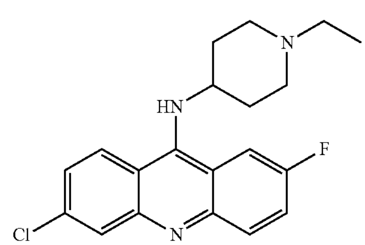 [SMILES: CCN1CCC(Nc2c3ccc(Cl)cc3nc3ccc(F)cc23)CC1] | 6-Chloro-N-(1-ethylpiperidin-4-yl)-2-fluoroacridin-9-amine |
| 17 | 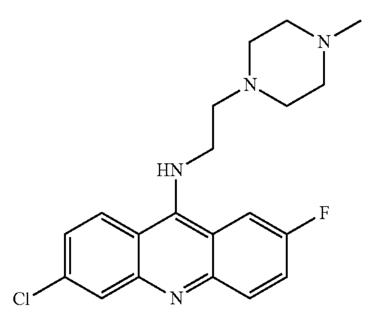 [SMILES: CN1CCN(CCNc2c3ccc(Cl)cc3nc3ccc(F)cc23)CC1] | 6-Chloro-2-fluoro-N-(2-(4-methylpiperazin-1-yl)ethyl)acridin-9-amine |

TABLE 1-continued

| Example | Structure | Name |
|---|---|---|
| 18 | 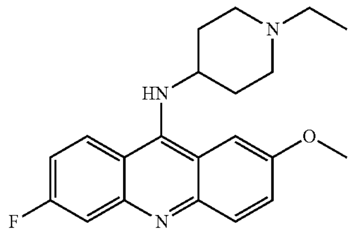 [SMILES: CCN1CCC(Nc2c3ccc(F)cc3nc3ccc(OC)cc23)CC1] | N-(1-Ethylpiperidin-4-yl)-6-fluoro-2-methoxyacridin-9-amine |
| 19 | 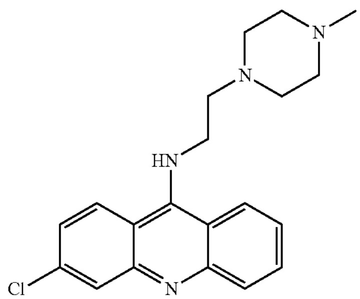 [SMILES: CN1CCN(CCNc2c3ccccc3nc3cc(Cl)ccc23)CC1] | 3-Chloro-N-(2-(4-methylpiperazin-1-yl)ethyl)acridin-9-amine |
| 20 | 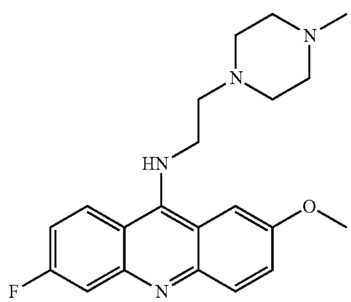 [SMILES: COc1ccc2nc3cc(F)ccc3c(NCCN3CCN(C)CC3)c2c1] | 6-Fluoro-2-methoxy-N-(2-(4-methylpiperazin-1-yl)ethyl)acridin-9-amine |
| 21 | 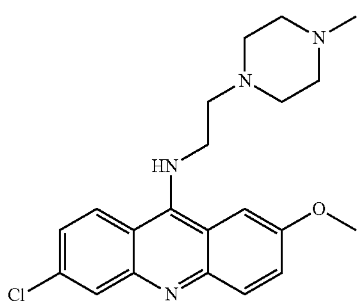 | 6-Chloro-2-methoxy-N-(2-(4-methylpiperazin-1-yl)ethyl)acridin-9-amine |
| 22 | 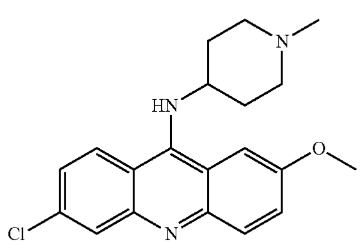 [SMILES: COc1ccc2nc3cc(Cl)ccc3c(NC3CCN(C)CC3)c2c1] | 6-Chloro-2-methoxy-N-(1-methylpiperidin-4-yl)acridin-9-amine |

TABLE 1-continued

| Example | Structure | Name |
|---|---|---|
| 23 | 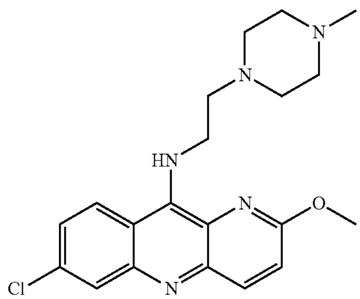 | 7-Chloro-2-methoxy-N-(2-(4-methylpiperazin-1-yl)ethyl)benzo[b][1,5]naphthyridin-10-amine |
| 24 | 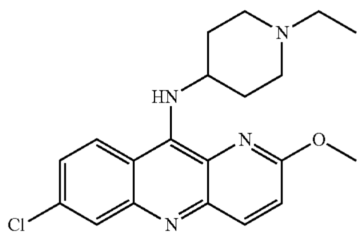 [SMILES: CCN1CCC(Nc2c3ccc(Cl)cc3nc3ccc(OC)nc23)CC1] | 7-Chloro-N-(1-ethylpiperidin-4-yl)-2-methoxybenzo[b][1,5]naphthyridin-10-amine |
| 25 | 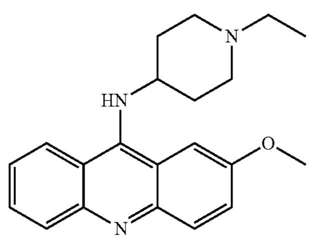 [SMILES: CCN1CCC(Nc2c3ccccc3nc3ccc(OC)cc23)CC1] | N-(1-Ethylpiperidin-4-yl)-2-methoxyacridin-9-amine |
| 26 | 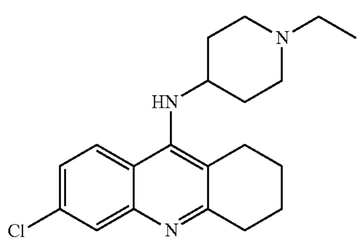 [SMILES: CCN1CCC(Nc2c3c(nc4cc(Cl)ccc24)CCCC3)CC1] | 6-Chloro-N-(1-ethylpiperidin-4-yl)-1,2,3,4-tetrahydroacridin-9-amine |
| 27 | 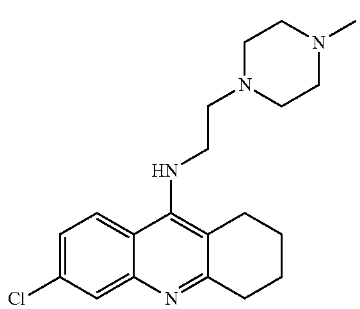 [SMILES: CN1CCN(CCNc2c3c(nc4cc(Cl)ccc24)CCCC3)CC1] | 6-Chloro-N-(2-(4-methylpiperazin-1-yl)ethyl)-1,2,3,4-tetrahydroacridin-9-amine |
| 28 | 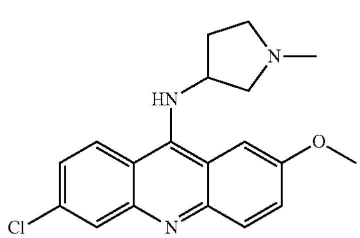 [SMILES: COc1ccc2nc3cc(Cl)ccc3c(NC3CCN(C)C3)c2c1] | 6-Chloro-2-methoxy-N-(1-methylpyrrolidin-3-yl)acridin-9-amine |

TABLE 1-continued

| Example | Structure | Name |
|---|---|---|
| 29 | 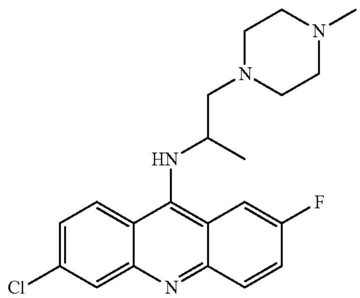 [SMILES: CC(CN1CCN(C)CC1)Nc1c2ccc(Cl)cc2nc2ccc(F)cc12] | 6-Chloro-2-fluoro-N-(1-(4-methylpiperazin-1-yl)propan-2-yl)acridin-9-amine |
| 30 | 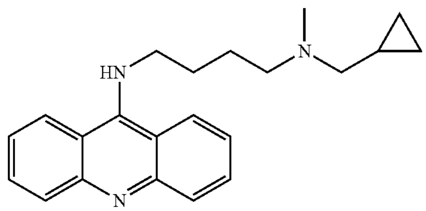 [SMILES: CN(CCCCNc1c2ccccc2nc2ccccc12)CC1CC1] | $N^1$-(acridin-9-yl)-$N^4$-(cyclopropylmethyl)-$N^4$-methylbutane-1,4-diamine |
| 31 | 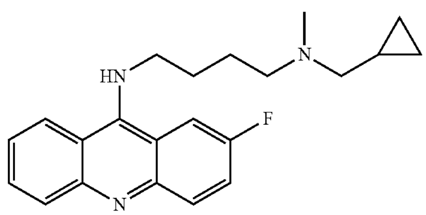 | $N^1$-(cyclopropylmethyl)-$N^4$-(2-fluoroacridin-9-yl)-$N^1$-methylbutane-1,4-diamine |
| 32 | 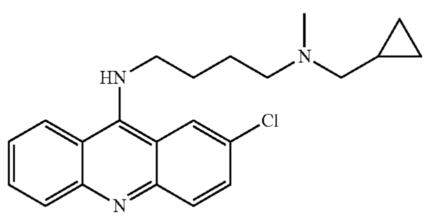 [SMILES: CN(CCCCNc1c2ccccc2nc2ccc(Cl)cc12)CC1CC1] | $N^1$-(2-chloroacridin-9-yl)-$N^4$-(cyclopropylmethyl)-$N^4$-methylbutane-1,4-diamine |
| 33 | 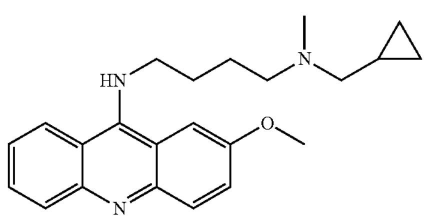 [SMILES: COc1ccc2nc3ccccc3c(NCCCCN(C)CC3CC3)c2c1] | $N^1$-(cyclopropylmethyl)-$N^4$-(2-methoxyacridin-9-yl)-$N^1$-methylbutane-1,4-diamine |
| 34 | 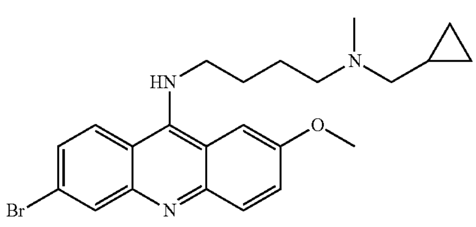 | $N^1$-(6-bromo-2-methoxyacridin-9-yl)-$N^4$-(cyclopropylmethyl)-$N^4$-methylbutane-1,4-diamine |
| 35 | 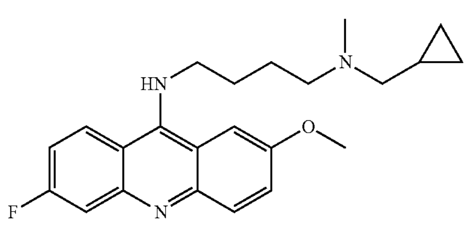 [SMILES: COc1ccc2nc3cc(F)ccc3c(NCCCCN(C)CC3CC3)c2c1] | $N^1$-(cyclopropyl-methyl)-$N^4$-(6-fluoro-2-methoxyacridin-9-yl)-$N^1$-methylbutane-1,4-diamine |

TABLE 1-continued

| Example | Structure | Name |
|---|---|---|
| 36 | 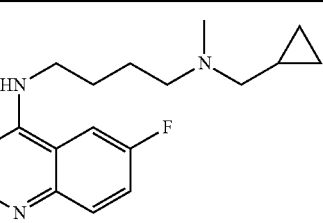 | $N^1$-(6-chloro-2-fluoroacridin-9-yl)-$N^4$-(cyclopropylmethyl)-$N^4$-methylbutane-1,4-diamine |
| 37 | 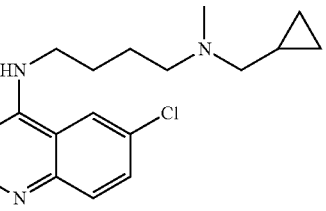 | $N^1$-(cyclopropylmethyl)-$N^4$-(2,6-dichloroacridin-9-yl)-$N^1$-methylbutane-1,4-diamine |
| 38 | 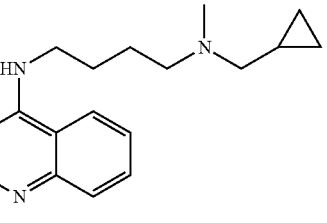 | $N^1$-(3-chloroacridin-9-yl)-$N^4$-(cyclopropylmethyl)-$N^4$-methylbutane-1,4-diamine |
| 39 | 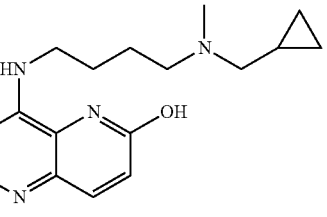 | 7-chloro-10-(4-((cyclopropylmethyl)(methyl)amino)butylamino)benzo[b][1,5]naphthyridin-2-ol |
| 40 | 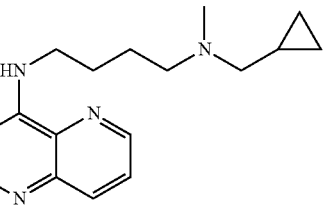 | $N^1$-(7-chlorobenzo[b][1,5]naphthyridin-10-yl)-$N^4$-(cyclopropylmethyl)-$N^4$-methylbutane-1,4-diamine |
| 41 | 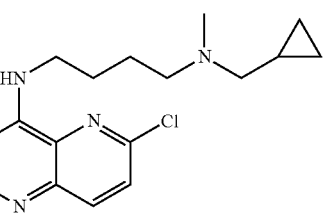 | $N^1$-(cyclopropylmethyl)-$N^4$-(2,7-dichlorobenzo[b][1,5]naphthyridin-10-yl)-$N^1$-methylbutane-1,4-diamine |
| 42 | 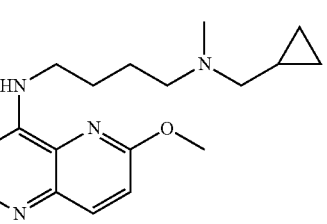 | $N^1$-(7-chloro-2-methoxybenzo[b][1,5]naphthyridin-10-yl)-$N^4$-(cyclopropylmethyl)-$N^4$-methylbutane-1,4-diamine |

TABLE 1-continued

| Example | Structure | Name |
|---|---|---|
| 43 | 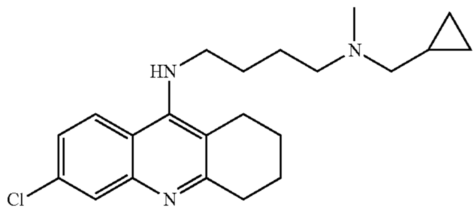 [SMILES: CN(CCCCNc1c2c(nc3cc(Cl)ccc13)CCCC2)CC1CC1] | $N^1$-(6-chloro-1,2,3,4-tetrahydroacridin-9-yl)-$N^4$-(cyclopropylmethyl)-$N^4$-methylbutane-1,4-diamine |
| 44 | 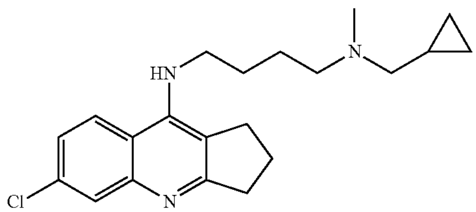 [SMILES: CN(CCCCNc1c2c(nc3cc(Cl)ccc13)CCC2)CC1CC1] | $N^1$-(6-chloro-2,3-dihydro-1H-cyclopenta[b]quinolin-9-yl)-$N^4$-(cyclopropylmethyl)-$N^4$-methylbutane-1,4-diamine |
| 45 | 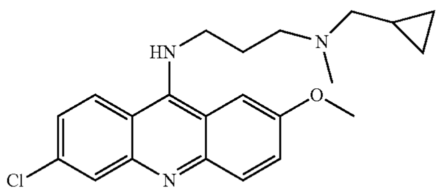 [SMILES: COc1ccc2nc3cc(Cl)ccc3c(NCCCN(C)CC3CC3)c2c1] | $N^1$-(6-chloro-2-methoxyacridin-9-yl)-$N^3$-(cyclopropylmethyl)-$N^3$-methylpropane-1,3-diamine |
| 46 | 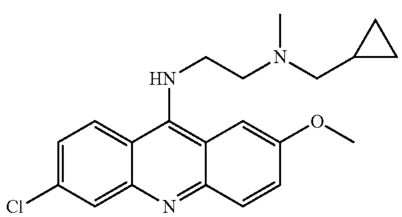 [SMILES: COc1ccc2nc3cc(Cl)ccc3c(NCCN(C)CC3CC3)c2c1] | $N^1$-(6-chloro-2-methoxyacridin-9-yl)-$N^2$-(cyclopropylmethyl)-$N^2$-methylethane-1,2-diamine |
| 47 | 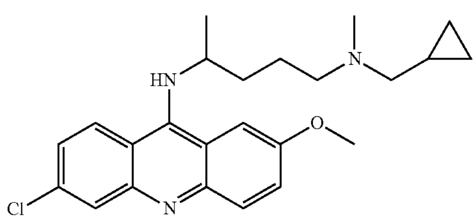 [SMILES: COc1ccc2nc3cc(Cl)ccc3c(NC(C)CCCN(C)CC3CC3)c2c1] | $N^4$-(6-chloro-2-methoxyacridin-9-yl)-$N^1$-(cyclopropylmethyl)-$N^1$-methylpentane-1,4-diamine |
| 48 | 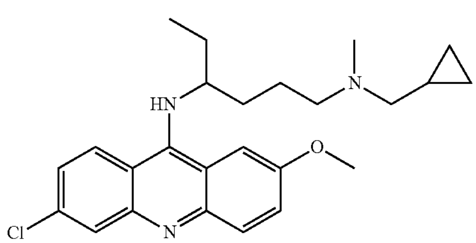 [SMILES: CCC(CCCN(C)CC1CC1)Nc1c2ccc(Cl)cc2nc2ccc(OC)cc12] | $N^4$-(6-chloro-2-methoxyacridin-9-yl)-$N^1$-(cyclopropylmethyl)-$N^1$-methylhexane-1,4-diamine |
| 49 | 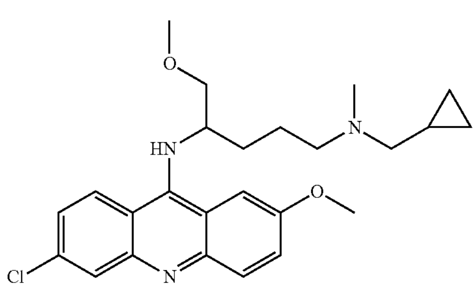 [SMILES: COCC(CCCN(C)CC1CC1)Nc1c2ccc(Cl)cc2nc2ccc(OC)cc12] | $N^4$-(6-chloro-2-methoxyacridin-9-yl)-$N^1$-(cyclopropylmethyl)-5-methoxy-$N^1$-methylpentane-1,4-diamine |

TABLE 1-continued

| Example | Structure | Name |
|---|---|---|
| 50 | 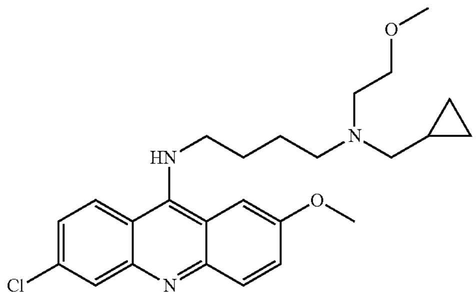 [SMILES: COCCN(CCCCNc1c2ccc(Cl)cc2nc2ccc(OC)cc12)CC1CC1] | $N^1$-(6-chloro-2-methoxyacridin-9-yl)-$N^4$-(cyclopropylmethyl)-$N^4$-(2-methoxyethyl)butane-1,4-diamine |
| 51 | 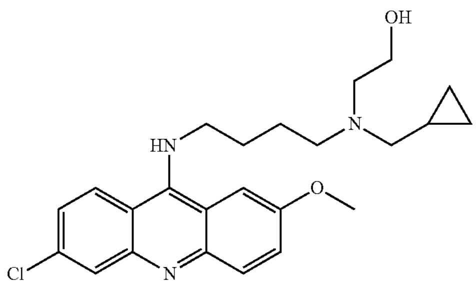 [SMILES: COc1ccc2nc3cc(Cl)ccc3c(NCCCCN(CCO)CC3CC3)c2c1] | 2-((4-(6-chloro-2-methoxyacridin-9-ylamino)butyl)(cyclopropylmethyl)amino)ethanol |
| 52 | 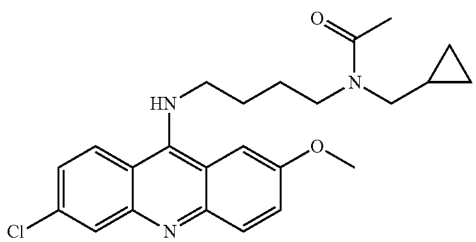 [SMILES: COc1ccc2nc3cc(Cl)ccc3c(NCCCCN(CC3CC3)C(C)=O)c2c1] | N-(4-(6-chloro-2-methoxyacridin-9-ylamino)butyl)-N-(cyclopropylmethyl)acetamide |
| 53 | 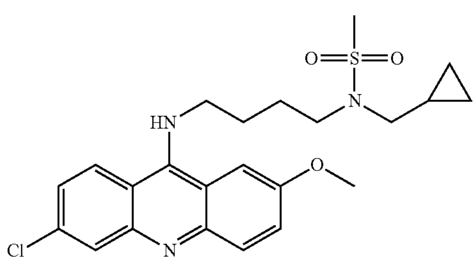 [SMILES: COc1ccc2nc3cc(Cl)ccc3c(NCCCCN(CC3CC3)S(C)(=O)=O)c2c1] | N-(4-(6-chloro-2-methoxyacridin-9-ylamino)butyl)-N-(cyclopropylmethyl)methanesulfonamide |
| 54 | 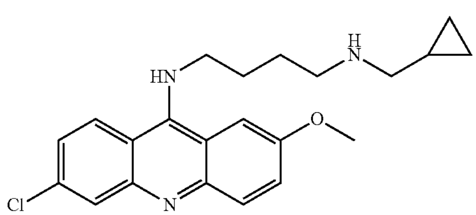 [SMILES: COc1ccc2nc3cc(Cl)ccc3c(NCCCCNCC3CC3)c2c1] | $N^1$-(6-chloro-2-methoxyacridin-9-yl)-$N^4$-(cyclopropylmethyl)butane-1,4-diamine |
| 55 | 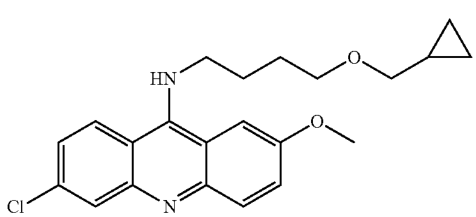 [SMILES: COc1ccc2nc3cc(Cl)ccc3c(NCCCCOCC3CC3)c2c1] | 6-chloro-N-(4-(cyclopropylmethoxy)butyl)-2-methoxyacridin-9-amine |

TABLE 1-continued

| Example | Structure | Name |
|---|---|---|
| 56 | 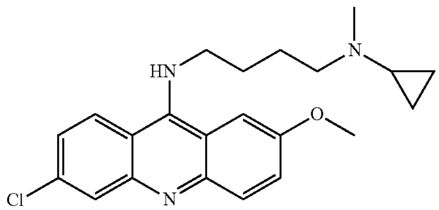 [SMILES: COc1ccc2nc3cc(Cl)ccc3c(NCCCCN(C)C3CC3)c2c1] | N¹-(6-chloro-2-methoxyacridin-9-yl)-N⁴-cyclopropyl-N⁴-methylbutane-1,4-diamine |
| 57 | 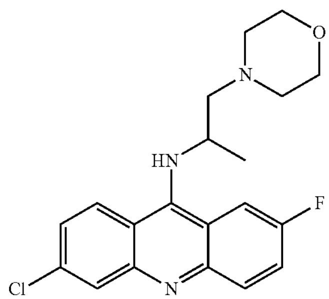 [SMILES: CC(CN1CCOCC1)Nc1c2ccc(Cl)cc2nc2ccc(F)cc12] | 6-chloro-2-fluoro-N-(1-morpholinopropan-2-yl)acridin-9-amine |
| 58 | 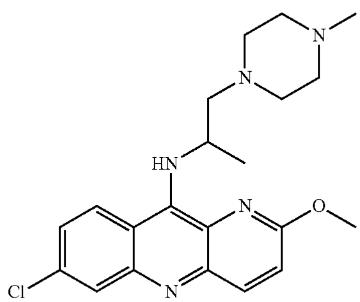 [SMILES: COc1ccc2nc3cc(Cl)ccc3c(NC(C)CN3CCN(C)CC3)c2n1] | 7-Chloro-2-methoxy-N-(1-(4-methylpiperazin-1-yl)propan-2-yl)benzo[b][1,5]naphthyridin-10-amine |
| 59 | 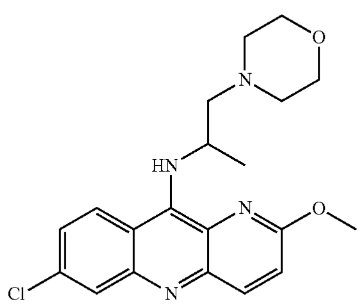 [SMILES: COc1ccc2nc3cc(Cl)ccc3c(NC(C)CN3CCOCC3)c2n1] | 7-Chloro-2-methoxy-N-(1-morpholinpropan-2-yl)benzo[b][1,5]naphthyridin-10-amine |
| 60 | 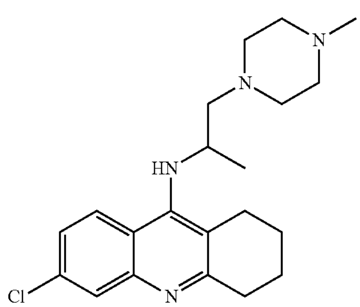 [SMILES: CC(CN1CCN(C)CC1)Nc1c2c(nc3cc(Cl)ccc13)CCCC2] | 6-Chloro-N-(1-(4-methylpiperazin-1-yl)propan-2-yl)-1,2,3,4-tetrahydroacridin-9-amine |

TABLE 1-continued

| Example | Structure | Name |
|---|---|---|
| 61 | 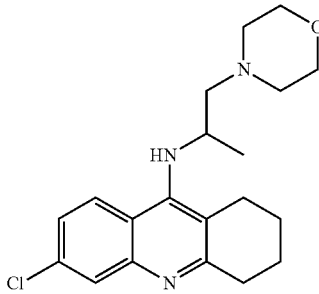 | 6-Chloro-N-(1-morpholinopropan-2-yl)-1,2,3,4-tetrahydroacridin-9-amine |
| 62 | 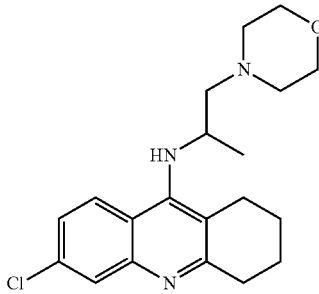 | 6-Chloro-N-(4-(4-methylpiperazin-1-yl)butan-2-yl)-1,2,3,4-tetrahydroacridin-9-amine |
| 63 | 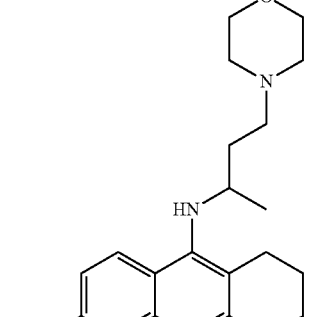 | 6-Chloro-N-(4-morpholinobutan-2-yl)-1,2,3,4-tetrahydroacridin-9-amine |
| 64 | 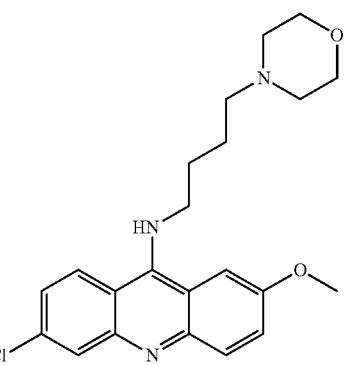 | 6-chloro-2-methoxy-N-(4-morpholinobutyl)acridin-9-amine |

The compounds of formulas III and V are amines and, as such, form salts when reacted with acids. Thus, pharmaceutically acceptable salts of compounds of formulas III and V are included within the scope of this invention. Pharmaceutically acceptable salts include salts of both inorganic and organic acids. The pharmaceutically acceptable salts are preferred over the corresponding free amines since they produce compounds that are more water soluble and more crystalline. Pharmaceutically acceptable salts are any salt which retains the activity of the parent compound and does not impart any deleterious or undesirable effect on the subject to whom it is administered and in the context in which it is administered. The preferred pharmaceutically acceptable salts include salts of the following acids acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, succinic, sulfamic, sulfanilic, sulfonic, sulfuric, tannic, tartaric, teoclic and toluenesulfonic. For other acceptable salts, see Int. J. Pharm., 33, 201-217 (1986) and J. Pharm. Sci., 66(1), 1, (1977).

In some aspects of the invention the disclosed compound, is in the form of a pharmaceutically acceptable salt. Pharmaceutically acceptable salts include any salt derived from an organic or inorganic acid. Examples of such salts include but are not limited to the following: salts of hydrobromic acid, hydrochloric acid, nitric acid, phosphoric acid, and sulphuric acid. Organic acid addition salts include, for example, salts of acetic acid, benzenesulphonic acid, benzoic acid, camphorsulphonic acid, citric acid, 2-(4-chlorophenoxy)-2-methylpropionic acid, 1,2-ethanedisulphonic acid, ethanesulphonic acid, ethylenediaminetetraacetic acid (EDTA), fumaric acid, glucoheptonic acid, gluconic acid, glutamic acid, N-glycolylarsanilic acid, 4-hexylresorcinol, hippuric acid, 2-(4-hydroxybenzoyl) benzoicacid, 1-hydroxy-2-naphthoicacid, 3-hydroxy-2-naphthoic acid, 2-hydroxyethanesulphonic acid, lactobionic acid, n-dodecyl sulphuric acid, maleic acid, malic acid, mandelic acid, methanesulphonic acid, methyl sulpuric acid, mucic acid, 2-naphthalenesulphonic acid, pamoic acid, pantothenic acid, phosphanilic acid ((4-aminophenyl) phosphonic acid), picric acid, salicylic acid, stearic acid, succinic acid, tannic acid, tartaric acid, terephthalic acid, p-toluenesulphonic acid, 10-undecenoic acid, or any other such acid now known or yet to be disclosed. It will be appreciated by one skilled in the art that such pharmaceutically acceptable salts may be used in the formulation of a pharmacological composition. Such salts may be prepared by reacting the disclosed compounds with a suitable acid in a manner known by those skilled in the art.

Pharmaceutically acceptable anion salts include, but are not limited to, salts of the following acids: methanesulfonic, hydrochloric, hydrobromic, sulfuric, phosphoric, nitric, benzoic, citric, tartaric, fumaric, maleic, $CH_3$—$(CH_2)_n$—COOH where n is 0 through 4, and HOOC—$(CH_2)N$—COOH where n is as defined above.

Processes for Making Compounds of Formula III or V

The compounds of formula III or V are prepared from known compounds by methods known to those skilled in the art. Thus a compound of formula III is prepared from the corresponding compound of formula I by coupling with an amine of formula II, as depicted in Scheme 1.

Scheme 1

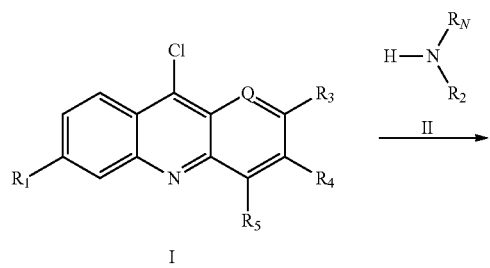

-continued

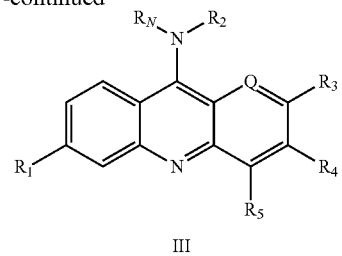

III

Similarly, the compound of formula V is prepared by from the corresponding compound of formula N by coupling with an amine of formula II, as depicted in Scheme 2:

Scheme 2

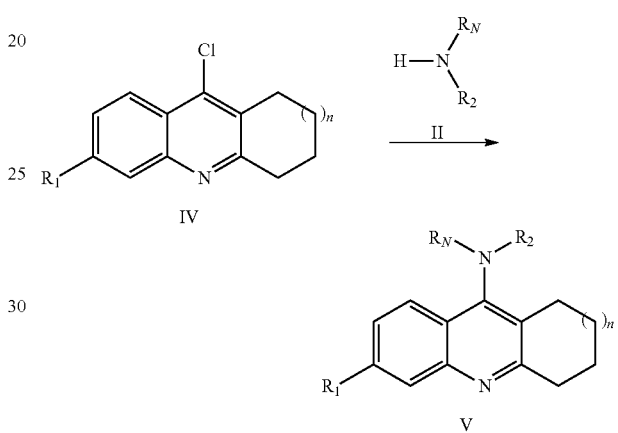

To the extent that some of the halides of formula I, the amines of formula II, and the halides of formula IV are not known compounds, they can be readily prepared from known compounds by methods known to those skilled in the art.

More specifically, the halides of formulas I and IV are heated to about 100° C. in a solvent like phenol. To this mixture, the desired amine (II) is added, and the mixture is kept at about 100° C. for about 5 hours. The mixture is cooled, diluted with a solvent such as dichloromethane, and is worked up as is known to those skilled in the art. Example 1 illustrates the process.

Pharmaceutical Compositions and Formulations

In another aspect, the invention further provides pharmaceutical compositions that include the compounds of formula III or V as the active pharmaceutical ingredient(s). Such pharmaceutical compositions may take any physical form necessary depending on a number of factors including the desired method of administration and the physicochemical and stereochemical form taken by the compound or pharmaceutically acceptable salts of the compound. The concept of a pharmaceutical composition including compounds of formulas III and V also encompasses the compounds or a pharmaceutically acceptable salt thereof without any other additive. The physical form of the invention may affect the route of administration, and one skilled in the art would know to choose a route of administration that takes into consideration both the physical form of the compound and the disorder to be treated. Pharmaceutical compositions are prepared using known methods.

A pharmaceutical composition may include a second effective compound of a distinct chemical formula from the compounds of formula III or V. This second effective compound may have the same or a similar molecular target or it may act upstream or downstream of the molecular target of the compounds of formula III or V with regard to one or more biochemical pathways.

Pharmaceutical compositions including the compounds of formula III or V include materials capable of modifying the physical form of a dosage unit. In one example, the composition may a material that forms a coating that surrounds and/or contains the pharmaceutical composition. Materials that may be used in such a coating, include, for example, sugar, shellac, gelatin, or any other inert coating agent.

Pharmaceutical compositions of the compounds of formula III or V can be prepared as a gas or aerosol. Aerosols encompass a variety of systems including colloids and pressurized packages. Delivery of a composition in this form may include propulsion of a pharmaceutical composition including the disclosed compound through use of liquefied gas or other compressed gas or by a suitable pump system. Aerosols may be delivered in single phase, bi-phasic, or tri-phasic systems.

In some aspects of the invention, the compounds of formula III or V of the pharmaceutical composition are in the form of a solvate. Such solvates are produced by the dissolution of the disclosed compound in a pharmaceutically acceptable solvent. Pharmaceutically acceptable solvents include any mixtures of more than one solvent. Such solvents may include propan-1-ol, ethyl oleate, ethyl lactate, ethylene oxide, water, ethanol, and any other solvent that delivers a sufficient quantity of the disclosed compound to treat the affliction without serious complications arising from the use of the solvent in patients.

Pharmaceutical compositions also include a pharmaceutically acceptable carrier. Carriers include any substance that may be administered with the compounds of formula III or V with the intended purpose of facilitating, assisting, or helping the administration or other delivery of the compound. Carriers include any liquid, solid, semisolid, gel, aerosol or anything else that may be combined with the active compound to aid in its administration. Examples of carriers include diluents, adjuvants, excipients, water, and oils (including petroleum, animal, vegetable or synthetic oils). Such carriers include particulates such as a tablet or powder, liquids such as an oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or diglycerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition can take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, or elixirs. Examples include local infusion during surgery; topical application, by local injection; by a catheter; by a suppository; or by an implant. Administration can be by direct injection at the site (or former site) of a cancer, tumor, or precancerous tissue or into the central nervous system by any suitable route, including intraventricular and intrathecal injection. Intraventricular injection may be facilitated by an intraventricular catheter, for example, attached to a reservoir, such as an Ommaya reservoir. Pulmonary administration may be achieved by any of a number of methods known in the art. Examples include use of an inhaler or nebulizer, formulation with an aerosolizing agent, or via perfusion in a fluorocarbon or synthetic pulmonary surfactant. The compound of formula III or V can be delivered in the context of a vesicle such as a liposome or any other natural or synthetic vesicle.

A pharmaceutical composition formulated so as to be administered by injection may be prepared by dissolving the disclosed compound with water so as to form a solution. In addition, a surfactant may be added to facilitate the formation of a homogeneous solution or suspension. Surfactants include any complex capable of non-covalent interaction with the active ingredient so as to facilitate dissolution or homogeneous suspension of the compound.

Pharmaceutical compositions can be prepared in a form that facilitates topical or transdermal administration. Such preparations may be in the form of a solution, emulsion, ointment, gel base, transdermal patch or iontophoresis device. Examples of bases used in such compositions include opetrolatum, lanolin, polyethylene glycols, beeswax, mineral oil, diluents such as water and alcohol, and emulsifiers and stabilizers, thickening agents, or any other suitable base now known or yet to be disclosed.

In some embodiments, the compounds of formula III or V may be used in combination with additional agents. More particularly, the additional agent may be temozolomide or PLX-4032.

Examples of pharmaceutical compositions that may be used in combination with the compounds of formula III or V include nucleic acid binding compositions such as cis-diamminedichloro platinum (H) (cisplatin), doxorubicin, 5-fluorouracil, taxol, and topoisomerase inhibitors such as etoposide, teniposide, irinotecan and topotecan. Still other pharmaceutical compositions include antiemetic compositions such as metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron.

Still other examples of pharmaceutical compositions that can be used in combination with a pharmaceutical composition of the compounds of formula III or V are hematopoietic colony stimulating factors. Examples of hematopoietic colony stimulating factors include, but are not limited to, filgrastim, sargramostim, molgramostim and epoietin alfa. Alternatively, the pharmaceutical composition of the compounds of formula III or V can be used in combination with an anxiolytic agent. Examples of anxiolytic agents include, but are not limited to, buspirone, and benzodiazepines such as diazepam, lorazepam, oxazapam, chlorazepate, clonazepam, chlordiazepoxide and alprazolam.

Pharmaceutical compositions that may be used in combination with pharmaceutical compositions that include the compounds of formula III or V can include analgesic agents. Such agents may be opioid or non-opioid analgesic. Nonlimiting examples of opioid analgesics include morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofenac, diflusinal, etodolac, fenoprofen, flurbiprofen, ibuprofen, ketoprofen, indomethacin, ketorolac, meclofenamate, mefanamic acid, nabumetone, naproxen, piroxicam, sulindac or any other analgesic.

In other aspects of the invention, pharmaceutical compositions of the compounds of formula III or V can be used in combination with a method that involves treatment of cancer ex vivo. One example of such a treatment is an autologous stem cell transplant. In this method, a diseased entity's autologous hematopoietic stem cells are harvested and purged of all cancer cells. A therapeutic amount of a pharmaceutical composition including the compounds of formula III or V can then be administered to the patient prior to restoring the entity's bone marrow by addition of either the patient's own or donor stem cells.

Methods

Another aspect is a method treating a condition or disease, comprising administering to a subject in need of such treatment a compound or pharmaceutical composition of a compound of formula III or V.

In some embodiments, the disorder or disease is cancer, neurodegenerative disorders, autoimmune disorders, cardiovascular disorders, metabolic disorders, hamartoma syndrome, genetic muscle disorders, and myopathies.

In another aspect, the invention provides a method of treating cancer, comprising administrating to a patient in need of such treatment (e.g., a human patient) a compound of formula II or V, a pharmaceutically salt thereof or a pharmaceutical composition comprising a compound of formula III or V.

Cancers that may be treated by pharmaceutical compositions including the compounds of formula III or V either alone or in combination with another treatment modality include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Addition of a pharmaceutical composition to cancer cells includes all actions by which an effect of the pharmaceutical composition on the cancer cell is realized. The type of addition chosen will depend upon whether the cancer cells are in vivo, ex vivo, or in vitro, the physical or chemical properties of the pharmaceutical composition, and the effect the composition is to have on the cancer cell. Nonlimiting examples of addition include addition of a solution including the pharmaceutical composition to tissue culture media in which in vitro cancer cells are growing; any method by which a pharmaceutical composition may be administered to an animal including intravenous, per os, parenteral, or any other of the methods of administration; or the activation or inhibition of cells that in turn have effects on the cancer cells such as immune cells (e.g. macophages and CD8+ T cells) or endothelial cells that may differentiate into blood vessel structures in the process of angiogenesis or vasculogenesis.

Determination of an effective amount of the compounds of formula III or V is within the capability of those skilled in the art, especially in light of the detailed disclosure provided herein. The effective amount of a pharmaceutical composition used to effect a particular purpose as well as its toxicity, excretion, and overall tolerance is determined in cell cultures or animals by pharmaceutical and toxicological procedures. One example is the determination of the IC50 (half maximal inhibitory concentration) of the pharmaceutical composition in vitro in cell lines or target molecules. Another example is the determination of the LD50 (lethal dose causing death in 50% of the tested animals) of the pharmaceutical composition in experimental animals. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition is well known to one of skill in the art who will use data obtained from any tests in making that determination. Determination of an effective amount of the compounds of formula III or V for addition to a cancer cell also includes the determination of an effective therapeutic amount, including the formulation of an effective dose range for use in vivo, including in humans.

The toxicity and therapeutic efficacy of a pharmaceutical composition may be determined by standard pharmaceutical procedures in cell cultures or animals. Examples include the determination of the IC50 (the half maximal inhibitory concentration) and the LD50 (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized.

The effective amount of compound of formula III or V to result in the slowing of expansion of the cancer cells would preferably result in a concentration at or near the target tissue that is effective in slowing cellular expansion in neoplastic cells, but have minimal effects on non-neoplastic cells, including non-neoplastic cells exposed to radiation or recognized chemotherapeutic chemical agents. Concentrations that produce these effects can be determined using, for example, apoptosis markers such as the apoptotic index and/or capsase activities either in vitro or in vivo.

The addition of a therapeutically effective amount of the compounds of formula III or V encompasses any method of dosing of a compound. Dosing of the disclosed compound may include single or multiple administrations of any of a number of pharmaceutical compositions that include the disclosed compound as an active ingredient. Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A final dosing regimen including the regularity of and mode of administration will be dependent on any of a number of factors including but not limited to the subject being treated; the severity of the affliction; the manner of administration, the stage of disease development, the presence of one or more other conditions such as pregnancy, infancy, or the presence of one or more additional diseases that affects the choice of the mode of administration, the dose to be administered and the time period over which the dose is administered.

Pharmaceutical compositions that include the compounds of formula III or V may be administered prior to, concurrently with, or after administration of a second pharmaceutical composition that may or may not include the compound. If the compositions are administered concurrently, they are administered within one minute of each other. If not administered concurrently, the second pharmaceutical composition may be administered a period of one or more minutes, hours, days, weeks, or months before or after the pharmaceutical composition that includes the compound.

Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration, in order to reduce the development of resistance to one or more of the compositions, to avoid or reduce the side effects of one or more of the compositions, and/or to improve the efficacy of the treatment.

The invention further encompasses kits that facilitate the administration of the disclosed compound to a diseased entity. An example of such a kit includes one or more unit dosages of the compounds of formula III or V. The unit dosage would be enclosed in a preferably sterile container and would be comprised of the compound(s) of formula III and V and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the device comprises the container that encloses the unit dosage.

Pharmaceutical compositions of the compounds of formula III or V are used in methods of treating cancer. Such methods involve the administration of a therapeutic amount of a pharmaceutical composition of the compound of formula III or V and/or a pharmaceutically acceptable salt thereof to a mammal in which a cancer has been diagnosed.

A therapeutic amount further includes the prevention of progression of the cancer to a neoplastic, malignant or metastatic state. Such preventative use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68-79). Hyperplasia is a form of controlled cell proliferation involving an increase in cell number in a tissue or organ, without significant alteration in structure or activity. For example, endometrial hyperplasia often precedes endometrial cancer and pre-cancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype or of a malignant phenotype, displayed in vivo or displayed in vitro by a cell sample derived from a patient can indicate the desirability of prophylactic/therapeutic administration of the pharmaceutical composition that includes the compound. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype). Further examples include leukoplakia, in which a benign-appearing hyperplastic or dysplastic lesion of the epithelium, or Bowen's disease, a carcinoma in situ, are pre-neoplastic lesions indicative of the desirability of prophylactic intervention. In another example, fibrocystic disease including cystic hyperplasia, mammary dysplasia, adenosis, or benign epithelial hyperplasia is indicates desirability of prophylactic intervention.

In some aspects of the invention, use of the disclosed compounds may be determined by one or more physical factors such as tumor size and grade or one or more molecular markers and/or expression signatures that indicate prognosis and the likely response to treatment with the compound. For example, determination of estrogen (ER) and progesterone (PR) steroid hormone receptor status has become a routine procedure in assessment of breast cancer patients. See, for example, Fitzgibbons et al, Arch. Pathol. Lab. Med. 124:966-78, 2000. Tumors that are hormone receptor positive are more likely to respond to hormone therapy and also typically grow less aggressively, thereby resulting in a better prognosis for patients with ER+/PR+ tumors. In a further example, overexpression of human epidermal growth factor receptor 2 (HER-2/neu), a transmembrane tyrosine kinase receptor protein, has been correlated with poor breast cancer prognosis (see, e.g., Ross et al, The Oncologist 8:307-25, 2003), and Her-2 expression levels in breast tumors are used to predict response to the anti-Her-2 monoclonal antibody therapeutic trastuzumab (Herceptin®, Genentech, South San Francisco, Calif.).

In another aspect of the invention, the diseased entity exhibits one or more predisposing factors for malignancy that may be treated by administration of a pharmaceutical composition including the compound. Such predisposing factors include but are not limited to chromosomal translocations associated with a malignancy such as the Philadelphia chromosome for chronic myelogenous leukemia and t (14; 18) for follicular lymphoma; an incidence of polyposis or Gardner's syndrome that are indicative of colon cancer; benign monoclonal gammopathy which is indicative of multiple myeloma, kinship with persons who have had or currently have a cancer or precancerous disease, exposure to carcinogens, or any other predisposing factor that indicates in increased incidence of cancer now known or yet to be disclosed.

The invention further encompasses methods of treating cancer that comprise combination therapies that comprise the administration of a pharmaceutical composition including the disclosed compound and another treatment modality. Such treatment modalities include but are not limited to, radiotherapy, chemotherapy, surgery, immunotherapy, cancer vaccines, radioimmunotherapy, treatment with pharmaceutical compositions other than those which include the compounds of formula III or V, or any other method that effectively treats cancer in combination with the compounds of formula III or V. Combination therapies may act synergistically. That is, the combination of the two therapies is more effective than either therapy administered alone. This results in a situation in which lower dosages of both treatment modality may be used effectively. This in turn reduces the toxicity and side effects, if any, associated with the administration either modality without a reduction in efficacy.

In another aspect of the invention, the pharmaceutical composition including the compounds of formula III or V is administered in combination with a therapeutically effective amount of radiotherapy. The radiotherapy may be administered concurrently with, prior to, or following the administration of the pharmaceutical composition including the compound. The radiotherapy may act additively or synergistically with the pharmaceutical composition including the compound. This particular aspect of the invention would be most effective in cancers known to be responsive to radiotherapy. Cancers known to be responsive to radiotherapy include, but are not limited to, Non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophogeal cancer, rectal cancer, small-cell lung cancer, non-small cell lung cancer, brain tumors, other CNS neoplasms, or any other such tumor.

Additional cancers that can be treated by pharmaceutical compositions of the compounds of formula III or V include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

The compounds of formula III or V can be used to treat cancer and to treat neurodegenerative disorders, auto-immune disorders, cardiovascular disorders, metabolic disorders, hamartoma syndrome, genetic muscle disorders, and myopathy. It is to be understood that each of the compounds of formulas III and V as recited herein are useful for a number of the above conditions, but not each and every compound is useful for each and every condition. It is well within the ability of those skilled in the art to easily determine which particular compound of formula III or V is useful for each particular condition without undue experimentation.

Further, compounds of formulas III and V can be used as cytostatic adjuvants to most small molecule/chemotherapy regimens, but the compounds also can be used as single agents. The compounds of formulas III and V can thus be used in combination with other drugs.

Determination of an effective amount of the disclosed compounds is within the capability of those skilled in the art, especially in light of the detailed disclosure provided herein. The effective amount of a pharmaceutical composition used to effect a particular purpose, as well as its toxicity, excretion, and overall tolerance is determined in cell cultures, or animals by pharmaceutical and toxicological procedures known to those skilled in the art. For example, in clinical practice the compounds of formula III and V will normally be administered 1-4 times daily; orally, rectally, parenterally, or other route of administration in an appropriate pharmaceutical compositions containing the active ingredient either as a free base or as a pharmaceutically acceptable acid addition salt in association with one or more pharmaceutically acceptable carriers. Suitable daily doses of the compounds of formula III and V are from about 0.1 to about 100 mg/kg for oral administration, preferably from about 0.5 to about 50 mg/kg, and from about 0.01 to about 50 mg/kg for parenteral administration, preferably from about 0.03 to about 3 mg/kg. The use and administration to a patient to be treated in the clinic would be readily apparent to a person of ordinary skill in the art.

The exact dosage and frequency of administration depends on the particular compound of formula III or V used, the particular condition being treated, the severity of the condition being treated, the age, weight, general physical condition of the particular patient, other medication the individual may be taking as is well known to those skilled in the art and can be more accurately determined by measuring the blood level or concentration of the compound of formula III or V in the patient's blood and/or the patients response to the particular condition being treated.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

6-Chloro-N-(1-ethylpiperidin-4-yl)-2-methoxyacridin-9-amine

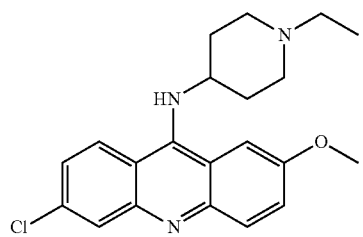 [SMILES: CCN1CCC(Nc2c3ccc(Cl)cc3nc3ccc(OC)cc23)CC1]

A mixture of 6,9-dichloro-2-methoxyacridine (100 mg, 0.36 mmol) and phenol (approximately 1.5 g) was heated to 100° C. under nitrogen atmosphere and stirred for 1 hour. 1-Ethylpiperidin-4-amine (92 mg, 0.72 mmol) was added to the mixture. The reaction was stirred at 100° C. for 5 hours, cooled to 20-25° C., and diluted with dichloromethane. The mixture was washed twice with sodium hydroxide solution (1 N) and twice with ammonium chloride solution. The phases were separated, and the organic layer was dried and concentrated. The residue was purified by Biotage column chromatography using triethylamine (5%) and methanol (5 to 15%) in dichloromethane to give the title compound; MS (Found: M+1=370).

Example 2

6-Chloro-N-(2-(2-(diethylamino)ethoxy)ethyl)-2-methoxyacridin-9-amine

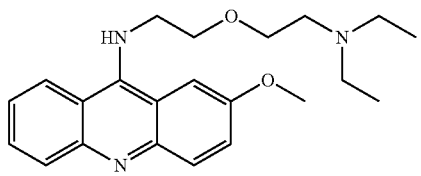 [SMILES: CCN(CC)CCOCCNc1c2ccccc2nc2ccc(OC)cc12]

Following the general procedure of Example 1 and making non-critical variations, but using 6,9-dichloro-2-methoxyacridine and commercially available 2-(2-aminoethoxy)-N,N-diethylethanamine, the title compound was obtained; MS (Found M+1=402).

Example 3

6-Chloro-2-methoxy-N-(4-methoxybutyl)acridin-9-amine

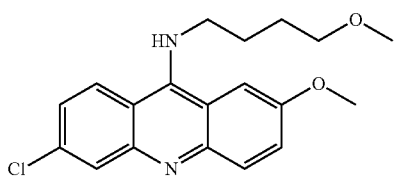 [SMILES: COCCCCNc1c2ccc(Cl)cc2nc2ccc(OC)cc12]

Following the general procedure of Example 1 and making non-critical variations, but using 6,9-dichloro-2-methoxyacridine and commercially available 4-methoxybutan-1-amine, the title compound was obtained; MS (Found M+1=345).

Example 4

6-Chloro-2-methoxy-N-(4-(pyrrolidin-1-yl)butyl)acridin-9-amine

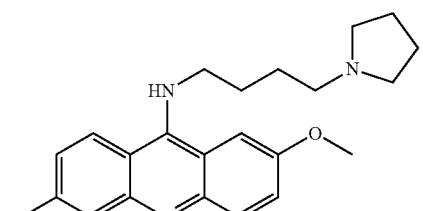

Step 1. Synthesis of 4-(benzyloxycarbonylamino)butyl methanesulfonate

To a solution of benzyl 4-hydroxybutylcarbamate (1.1 g, 4.9 mmol) and triethylamine (1.7 mL, 9.8 mmol) in THF was added methanesulfonyl chloride (0.67 g, 5.9 mmol) at 0° C. The reaction was stirred at 20-25° C. for 6 hours and concentrated. The residue was partitioned between ethyl acetate and water. The phases were separated, and the organic layer was washed with hydrochloride solution (1 N), saturated sodium bicarbonate solution, and saline. The separated organic layer was dried and concentrated to give 4-(benzyloxycarbonylamino)butyl methanesulfonate (1.2 g).

Step 2. Synthesis of benzyl 4-(pyrrolidin-1-yl)butylcarbamate

To a pressure vessel was added 4-(benzyloxycarbonylamino)butyl methanesulfonate (330 mg, 1.10 mmol) and pyrrolidine (234 mg, 3.3 mmol) in THF. The reaction was heated to 100° C., stirred overnight, cooled to 20-25° C., and concentrated. The crude concentrate was purified by Biotage column chromatography to give benzyl 4-(pyrrolidin-1-yl)butylcarbamate (200 mg).

Step 3. Synthesis of 4-(pyrrolidin-1-yl)butan-1-amine

To a solution of benzyl 4-(pyrrolidin-1-yl)butylcarbamate (196 mg, 0.71 mmol) was added catalytic amount of Pd/C (5%). The reaction was stirred under a hydrogen atmosphere overnight and filtered. The filtrate was concentrated to give 4-(pyrrolidin-1-yl)butan-1-amine (83 mg)

Step 4. Synthesis of the Title Compound

Following the general procedure of Example 1 and making non-critical variations, but using 6,9-dichloro-2-methoxyacridine and 4-(pyrrolidin-1-yl)butan-1-amine (Step 3), the title compound was obtained; MS (Found M+1=384).

Example 5

N[1]-tert-butyl-N[4]-(6-chloro-2-methoxyacridin-9-yl)butane-1,4-diamine

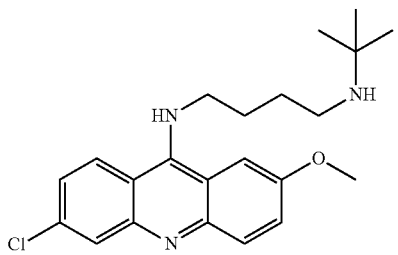 [SMILES: COc1ccc2nc3cc(Cl)ccc3c(NCCCCNC(C)(C)C)c2c1]

Following the general procedure of Example 1 and making non-critical variations, but using 6,9-dichloro-2-methoxyacridine and commercially available N[1]-tert-butylbutane-1,4-diamine, the title compound was obtained; MS (Found M+1=386).

Example 6

N-(4-(6-Chloro-2-methoxyacridin-9-ylamino)butyl)-N-ethylmethanesulfonamide

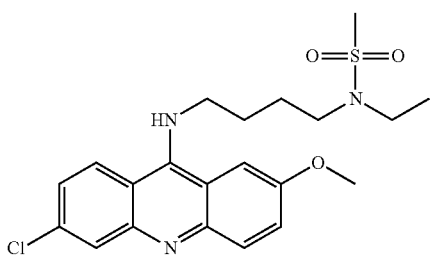 [SMILES: CCN(CCCCNc1c2ccc(Cl)cc2nc2ccc(OC)cc12)S(C)(=O)=O]

Step 1. Synthesis of benzyl 4-(ethylamino)butylcarbamate

Following the general procedure of Example 4, Step 2, and making non-critical variations but using 4-(benzyloxycarbonylamino)butyl methanesulfonate and ethyl amine in THF, the compound of Step 1 was obtained.

Step 2. Synthesis of benzyl 4-(N-ethylmethylsulfonamido)butylcarbamate

To a mixture of benzyl 4-(ethylamino)butylcarbamate (Step 1, 250 mg, 1.00 mmol) in dichloromethane was added pyridine (145 mg, 1.8 mmol) and then methanesulfonyl chloride (137 mg, 1.20 mmol) at 0° C. The reaction was stirred overnight and diluted with dichloromethane. The phases were separated, and the organic phase was washed with hydrochloride solution (1 N), saturated sodium bicarbonate and saline. The separated organic layer was concentrated and purified by Biotage column chromatography to give benzyl 4-(N-ethylmethylsulfonamido)butylcarbamate (231 mg).

Step 3. Synthesis of N-(4-aminobutyl)-N-ethylmethanesulfonamide

Following the general procedure of Example 4, Step 3, but using benzyl 4-(N-ethylmethylsulfonamido)butylcarbamate (Step 2), the compound of Step 3 was obtained.

Step 4. Synthesis of the Title Compound

Following the general procedure of Example 1 and making non-critical variations, but using 6,9-dichloro-2-methoxyacridine and N-(4-aminobutyl)-N-ethylmethanesulfonamide (Step 3), the title compound was obtained; MS (Found M+1=436).

Example 7

6-Chloro-2-methoxy-N-(4-(4-methylpiperazin-1-yl)butyl)acridin-9-amine

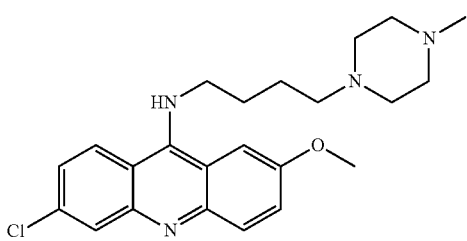 [SMILES: COc1ccc2nc3cc(Cl)ccc3c(NCCCCN3CCN(C)CC3)c2c1]

Following the general procedure of Example 1 and making non-critical variations, but using 6,9-dichloro-2-methoxyacridine and commercially available 4-(4-methylpiperazin-1-yl)butan-1-amine, the title compound was obtained, MS (Found M+1=413). $^1$H NMR (CD$_3$OD, 300 Hz): 8.32-8.30 (d, 1H J=8.2 Hz), 8.30-7.85 (m, 1H), 7.58-7.57 (d, 1H), 7.47-7.44 (m, 1H), 7.34-7.32 (m, 1H), 4.00 (s, 3H), 3.92-3.89 (t, 2H, J=6 Hz), 2.54-2.51 (b, 4H), 2.41-2.29 (m, 6H), 2.25 (s, 3H), 1.85-1.77 (m, 2H), 1.60-1.53 (m, 2H).

Example 8

3-Chloro-N-(1-ethylpiperidin-4-yl)acridin-9-amine

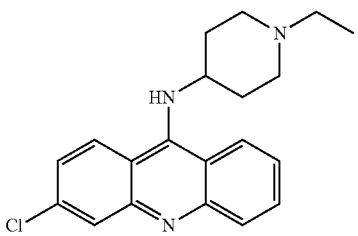 [SMILES: CCN1CCC(Nc2c3ccccc3nc3cc(Cl)ccc23)CC1]

Following the general procedure of Example 1 and making non-critical variations, but using 3,9-dichloroacridine (*J. Med. Chem.* 1985, 28. 940-944) and 1-ethylpiperidin-4-amine, the title compound was obtained; MS (Found M+1=340).

Example 9

N-(4-(6-Chloro-2-methoxyacridin-9-ylamino)butyl)-N-ethylacetamide

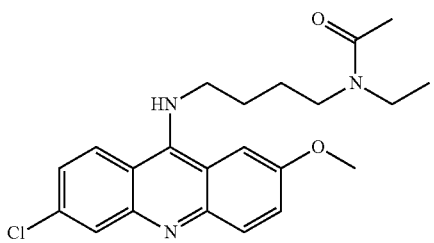 [SMILES: CCN(CCCCNc1c2ccc(Cl)cc2nc2ccc(OC)cc12)C(C)=O]

Step 1. Synthesis of N-(4-aminobutyl)-N-ethylacetamide

Following the general procedure of Example 6, Steps 2 and 3, and making non-critical variations N-(4-aminobutyl)-N-ethylacetamide was obtained.

Step 2. Synthesis of the Title Compound

Following the general procedure of Example 1, and making non-critical variations but using 6,9-dichloro-2-methoxyacridine and N-(4-aminobutyl)-N-ethylacetamide (Step 1), the title compound was obtained; MS (Found M+1=400).

Example 10

$N^1$-(6-Chloro-2-methoxyacridin-9-yl)-$N^4$-(cyclopropylmethyl)-$N^4$-methylbutane-1,4-diamine

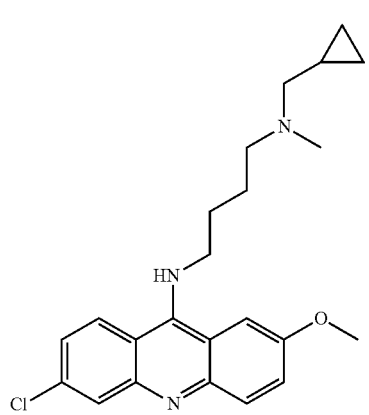

Step 1. Synthesis of $N^1$-(cyclopropylmethyl)-$N^1$-methylbutane-1,4-diamine Following the general procedure of Example 4, Steps 2 and 3, and making non-critical variations but using 4-(benzyloxycarbonylamino)butyl methanesulfonate and commercially available 1-cyclopropyl-N-methylmethanamine, $N^1$-(cyclopropylmethyl)-$N^1$-methylbutane-1,4-diamine was obtained.

Step 2. Synthesis of Title Compound

Following the general procedure of Example 1 and making non-critical variations but using 6,9-dichloro-2-methoxyacridine and $N^1$-(cyclopropylmethyl)-$N^1$-methylbutane-1,4-diamine (Step 1), the title compound was obtained; MS (Found M+1=398). $^1$H NMR (CDCl$_3$, 300 Hz): 8.05-7.94 (m, 3H), 7.40-7.36 (m, 1H), 7.26-7.23 (m, 2H), 3.93 (s, 3H), 3.75-3.71 (t, 2H, J=6 Hz), 2.48-2.43 (t, 2H, J=6 Hz), 2.29-2.22 (m, 5H), 1.85-1.78 (m, 2H), 1.76-1.65 (m, 2H), 0.87-0.85 (m, 1H), 0.50-0.45 (d, 2H, J=2.4 Hz), 0.09-0.05 (d, 2H, J=4.8 Hz).

Example 11

6-Chloro-2-methoxy-N-(2-methoxyethyl)acridin-9-amine

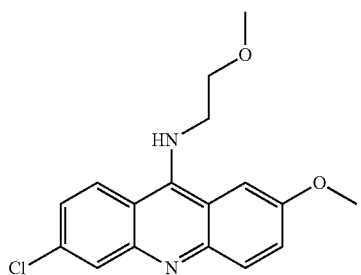 [SMILES: COCCNc1c2ccc(Cl)cc2nc2ccc(OC)cc12]

Following the general procedure of Example 1 and making non-critical variations but using 6,9-dichloro-2-methoxyacridine and 2-methoxyethanamine, the title compound was obtained; MS (Found M+1=317).

Example 12

$N^1$-(6-Chloro-2-methoxyacridin-9-yl)-$N^4$-cyclopropyl-$N^4$-ethylbutane-1,4-diamine

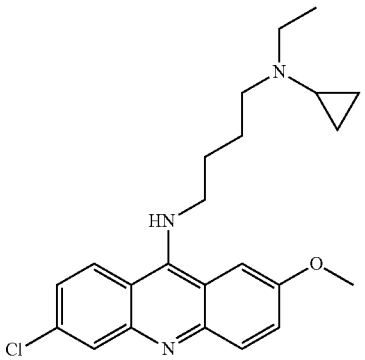 [SMILES: CCN(CCCCNc1c2ccc(Cl)cc2nc2ccc(OC)cc12)C1CC1]

Step 1. Synthesis of benzyl 4-(cyclopropyl(ethyl)amino)butylcarbamate

Following the general procedure of Example 4, Step 2, and making non-critical variations but using 4-(benzyloxycarbonylamino)butyl methanesulfonate and commercially available N-ethylcyclopropanamine, benzyl 4-(cyclopropyl(ethyl)amino)butylcarbamate was obtained.

Step 2. $N^1$-cyclopropyl-$N^1$-ethylbutane-1,4-diamine HCl Salt

The mixture of benzyl 4-(cyclopropyl(ethyl)amino)butylcarbamate (Step 1) in HCl (6 N) was heated to reflux for 1 hour and cooled to 20-25° C. The reaction mixture was concentrated, and the residue was dried under reduced pressure to give $N^1$-cyclopropyl-$N^1$-ethylbutane-1,4-diamine HCl salt.

Step 3. Synthesis of the Title Compound

Following the general procedure of Example 1 and making non-critical variations but using 6,9-dichloro-2-methoxyacridine, $N^1$-cyclopropyl-$N^1$-ethylbutane-1,4-diamine HCl salt (Step 2) and diisopropyethylamine (4 eq), the title compound was obtained; MS (Found M+1=398).

Example 13

$N^1$-(6-Chloro-2-methoxyacridin-9-yl)-$N^4$-(cyclopropylmethyl)-$N^4$-ethylbutane-1,4-diamine

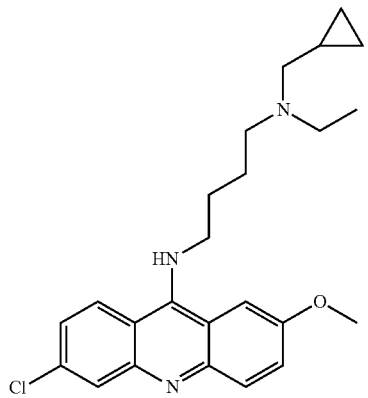 [SMILES: CCN(CCCCNc1c2ccc(Cl)cc2nc2ccc(OC)cc12)CC1CC1]

Step 1. Synthesis of $N^1$-(cyclopropylmethyl)-$N^1$-ethylbutane-1,4-diamine Following the general procedure of Example 4, Step 2, and making non-critical variations but using 4-(benzyloxycarbonylamino)butyl methanesulfonate and N-(cyclopropylmethyl)ethanamine, $N^1$-(cyclopropylmethyl)-$N^1$-ethylbutane-1,4-diamine was obtained

Step 2. Synthesis of the Title Compound

Following the general procedure of Example 1 and making non-critical variations but using 6,9-dichloro-2-methoxyacridine, $N^1$-(cyclopropylmethyl)-$N^1$-ethylbutane-1,4-diamine (Step 1), the title compound is obtained; MS (Found M+1=412).

Example 14

$N^1$-(6-Chloro-2-methoxyacridin-9-yl)-$N^4$,$N^4$-diethyl-$N^1$-methylbutane-1,4-diamine

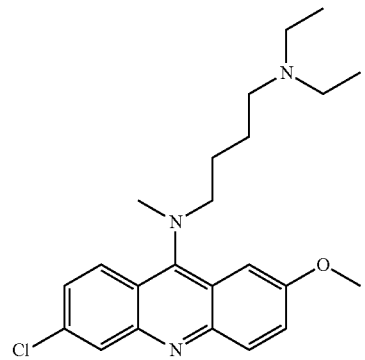 [SMILES: CCN(CC)CCCCN(C)c1c2ccc(Cl)cc2nc2ccc(OC)cc12]

Following the general procedure of Example 1 and making non-critical variations but using 6,9-dichloro-2-methoxyacridine and $N^1$,$N^1$-diethyl-$N^4$-methylbutane-1,4-diamine, the title compound was obtained; MS (Found M+1=400).

Example 15

N-(1-Ethylpiperidin-4-yl)acridin-9-amine

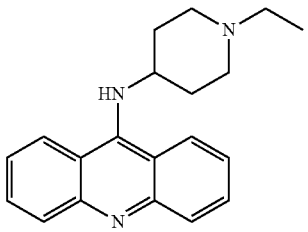 [SMILES: CCN1CCC(Nc2c3ccccc3nc3ccccc23)CC1]

Following the general procedure of Example 1 and making non-critical variations but using 9-chloroacridine and 1-ethylpiperidin-4-amine, the title compound was obtained; MS (Found M+1=306).

Example 16

6-Chloro-N-(1-ethylpiperidin-4-yl)-2-fluoroacridin-9-amine

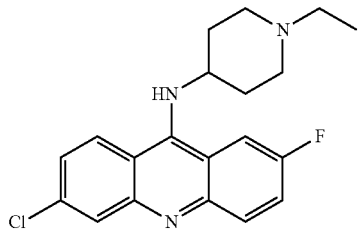 [SMILES: CCN1CCC(Nc2c3ccc(Cl)cc3nc3ccc(F)cc23)CC1]

Following the general procedure of Example 1 and making non-critical variations but using 6,9-dichloro-2-fluoroacridine (J. Med. Chem. 1985, 28. 940-944) and 1-ethylpiperidin-4-amine, the title compound was obtained; MS (Found M+1=358).

Example 17

6-Chloro-2-fluoro-N-(2-(4-methylpiperazin-1-yl)ethyl)acridin-9-amine

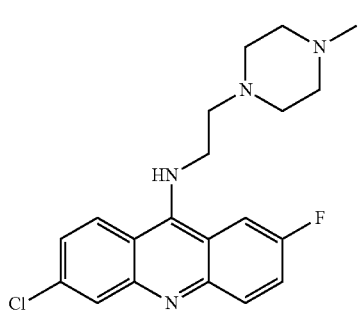 [SMILES: CN1CCN(CCNc2c3ccc(Cl)cc3nc3ccc(F)cc23)CC1]

Following the general procedure of Example 1 and making non-critical variations but using 6,9-dichloro-2-fluoroacridine and 2-(4-methylpiperazin-1-yl)ethanamine, the title compound was obtained; MS (Found M+1=373).

Example 18

N-(1-Ethylpiperidin-4-yl)-6-fluoro-2-methoxyacridin-9-amine

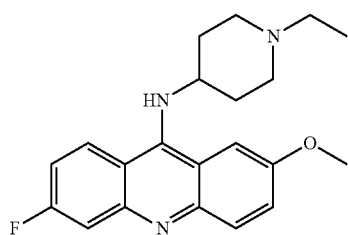 [SMILES: CCN1CCC(Nc2c3ccc(F)cc3nc3ccc(OC)cc23)CC1]

Following the general procedure of Example 1 and making non-critical variations but using 9-dichloro-6-fluoro-2-methoxyacridine and 1-ethylpiperidin-4-amine, the title compound was obtained; MS (Found M+1=354).

Example 19

3-Chloro-N-(2-(4-methylpiperazin-1-yl)ethyl)acridin-9-amine

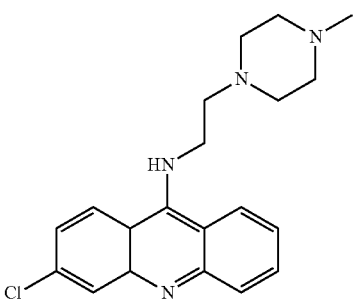 [SMILES: CN1CCN(CCNC2=c3ccccc3=NC3C=C(Cl)C=CC23)CC1]

Following the general procedure of Example 1 and making non-critical variations but using 3,9-dichloroacridine (*J. Med. Chem.* 1985, 28. 940-944) and 2-(4-methylpiperazin-1-yl)ethanamine, the title compound was obtained; MS (Found M+1=355).

Example 20

6-Fluoro-2-methoxy-N-(2-(4-methylpiperazin-1-yl)ethyl)acridin-9-amine

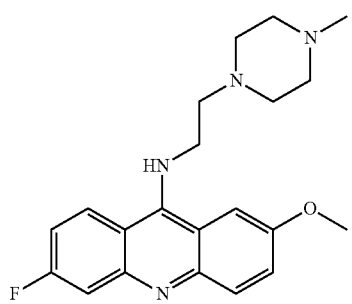 [SMILES: COc1ccc2nc3cc(F)ccc3c(NCCN3CCN(C)CC3)c2c1]

Following the general procedure of Example 1 and making non-critical variations but using 9-dichloro-6-fluoro-2-methoxyacridine and 2-(4-methylpiperazin-1-yl)ethanamine, the title compound was obtained; MS (Found M+1=369).

Example 21

6-Chloro-2-methoxy-N-(2-(4-methylpiperazin-1-yl)ethyl)acridin-9-amine

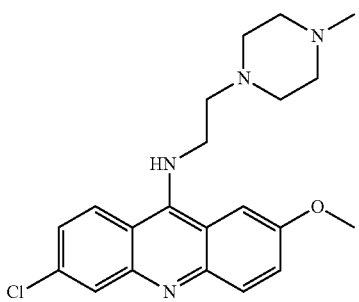 [SMILES: COc1ccc2nc3cc(Cl)ccc3c(NCCN3CCN(C)CC3)c2c1]

Following the general procedure of Example 1 and making non-critical variations but using 6,9-dichloro-2-methoxyacridine and 2-(4-methylpiperazin-1-yl)ethanamine, the title compound was obtained; MS (Found M+1=385).

Example 22

6-Chloro-2-methoxy-N-(1-methylpiperidin-4-yl)acridin-9-amine

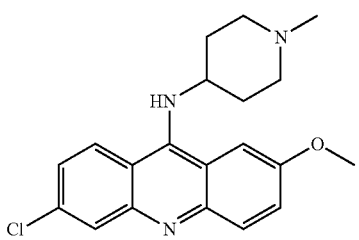 [SMILES: COc1ccc2nc3cc(Cl)ccc3c(NC3CCN(C)CC3)c2c1]

Following the general procedure of Example 1 and making non-critical variations but using 6,9-dichloro-2-methoxyacridine and 1-methylpiperidin-4-amine, the title compound was obtained; MS (Found M+1=356).

Example 23

7-Chloro-2-methoxy-N-(2-(4-methylpiperazin-1-yl)ethyl)benzo[b][1,5]naphthyridin-10-amine

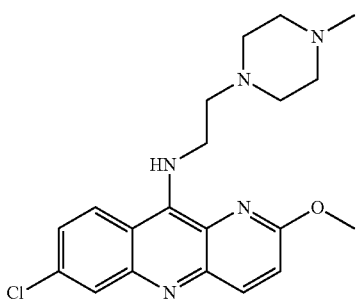 [SMILES: COc1ccc2nc3cc(Cl)ccc3c(NCCN3CCN(C)CC3)c2n1]

Following the general procedure of Example 1 and making non-critical variations but using 7,10-dichloro-2-methoxypyrido[3,2-b]quinoline and 2-(4-methylpiperazin-1-yl)ethanamine, the title compound was obtained; MS (Found M+1=386). ¹H NMR (DMSO-d6, 400 Hz): 8.43-8.41 (d, 1H, J=9.2 Hz), 8.12-8.10 (d, 1H, J=9.2 Hz), 7.87 (b, 1H), 7.2 (s, 1H), 7.2.9-7.27 (d, 1H, J=9.2 Hz) 7.25-7.24 (d, 1H, J=9.2 Hz), 4.10 (m, 2H), 4.06 (s, 3H), 2.70-2.68 (m, 2H), 2.33 (b, 8H), 2.14 (s, 3H).

Example 24

7-Chloro-N-(1-ethylpiperidin-4-yl)-2-methoxybenzo[b][1,5]naphthyridin-10-amine

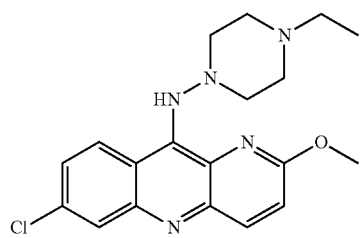

Following the general procedure of Example 1 and making non-critical variations but using 7,10-dichloro-2-methoxypyrido[3,2-b]quinoline and 1-ethylpiperidin-4-amine, the title compound was obtained; MS (Found M+1=371). ¹H NMR (DMSO-d6, 400 Hz): 8.43-8.42 (d, 1H, J=9.2 Hz), 8.11-8.10 (d, 1H, J=9.2 Hz), 7.84 (s, 1H), 7.37-7.35 (d, 1H, J=9.2 Hz) 7.25-7.23 (d, 1H, J=9.2 Hz), 6.95 (b, 1H), 4.98 (b, 1H), 4.00 (s, 3H), 2.85 (b, 2H), 2.30 (b, 2H), 2.02-1.99 (m 4H), 1.00-1.97 (t, 3H, J=7.2 Hz).

Example 25

N-(1-Ethylpiperidin-4-yl)-2-methoxyacridin-9-amine

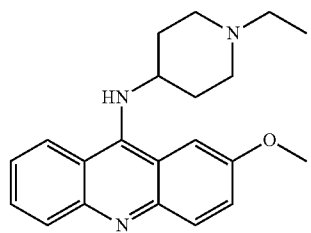 [SMILES: CCN1CCC(Nc2c3ccccc3nc3ccc(OC)cc23)CC1]

Following the general procedure of Example 1 and making non-critical variations but using 9-chloro-2-methoxyacridine and 1-ethylpiperidin-4-amine, the title compound was obtained; MS (Found M+1=336). ¹H NMR (CD₃OD, 400 Hz): 8.2.9-8.27 (d, 1H, J=8.8 Hz), 7.96-7.94 (d, 1H, J=8.8 Hz), 7.92-7.89 (d, 1H, J=9.6 Hz), 7.70-7.66 (m, 1H), 7.53 (m, 1H), 7.46-7.43 (m, 2H), 3.98 (s, 3H), 3.90-3.80 (m, 1H), 3.02-3.8 (bm, 2H), 2.46-2.41 (q, 2H, J=7.2 Hz), 2.05-2.00 (m, 4H), 1.93-1.83 (m, 2H), 1.11-1.08 (t, 3H, J=7.2 Hz).

Example 26

6-Chloro-N-(1-ethylpiperidin-4-yl)-1,2,3,4-tetrahydroacridin-9-amine

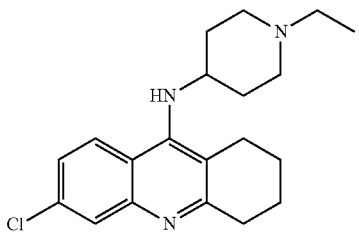 [SMILES: CCN1CCC(Nc2c3c(nc4cc(Cl)ccc24)CCCC3)CC1]

Following the general procedure of Example 1 and making non-critical variations but using 6,9-dichloro-1,2,3,4-tetrahydroacridine and 1-ethylpiperidin-4-amine, the title compound was obtained; MS (Found M+1=344).

Example 27

6-Chloro-N-(2-(4-methylpiperazin-1-yl)ethyl)-1,2,3,4-tetrahydroacridin-9-amine

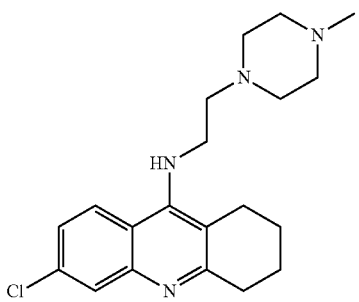 [SMILES: CN1CCN(CCNc2c3c(nc4cc(Cl)ccc24)CCCC3)CC1]

Following the general procedure of Example 1 and making non-critical variations but using 6,9-dichloro-1,2,3,4-tetrahydroacridine and 2-(4-methylpiperazin-1-yl)ethanamine, the title compound was obtained; MS (Found M+1=359). ¹H NMR (CDCl3, 300 Hz): 7.97-7.95 (m, 2H, J=9 Hz), 7.95-7.91 (d, 1H, J=9 Hz), 7.28-7.25 (m, 1H), 5.25 (b, 1H), 3.58-3.49 (m, 2H), 3.05 (m, 2H), 3.73 (m, 2H), 2.63-2.59 (m 10H), 2.39 (s, 3H), 1.94-1.90 (m, 4H).

Example 28

6-Chloro-2-methoxy-N-(1-methylpyrrolidin-3-yl)acridin-9-amine

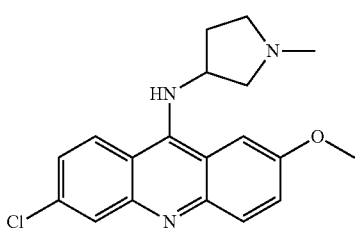 [SMILES: COc1ccc2nc3cc(Cl)ccc3c(NC3CCN(C)C3)c2c1]

Following the general procedure of Example 1 and making non-critical variations but using 6,9-dichloro-2-methoxyacridine and 1-methylpyrrolidin-3-amine, the title compound was obtained; MS (Found M+1=356)

Example 29

6-Chloro-2-fluoro-N-(1-(4-methylpiperazin-1-yl)propan-2-yl)acridin-9-amine

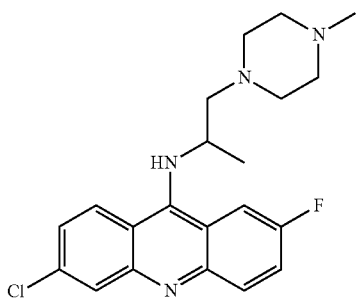 [SMILES: CC(CN1CCN(C)CC1)Nc1c2ccc(Cl)cc2nc2ccc(F)cc12]

Following the general procedure of Example 1 and making non-critical variations and starting with the appropriate starting materials, the title compound was obtained.

Examples 30-56 in Table 1 were prepared according to the above examples using appropriate starting materials. MS data is summarized for the compounds in Table 2.

TABLE 2

| Example | MS m/z (M + 1) |
|---|---|
| 30 | 334.2 |
| 31 | 352.1 |
| 32 | 368.2 |
| 33 | 364.2 |
| 34 | 443.3 |
| 35 | 382.1 |
| 36 | 386.1 |
| 37 | 403.1 |
| 38 | 368.2 |
| 39 | 385.1 |
| 40 | 369.2 |
| 41 | 403.2 |
| 42 | 399.2 |
| 43 | 372.1 |
| 44 | 358.1 |
| 45 | 384.2 |
| 46 | 370.2 |
| 47 | 412.2 |
| 48 | 426.2 |
| 49 | 442.1 |
| 50 | 442.1 |
| 51 | 428.2 |
| 52 | 426.2 |
| 53 | 462.1 |
| 54 | 384.2 |
| 55 | 385.1 |
| 56 | 384.1 |
| 64 | 400.0 |

Biological Example 1

Tumor cell lines (H292, HCT116, A375, HCC1569, A498, N87, UACC1093, and UACC647) were cultured in RPMI 1640 supplemented with 5% fetal bovine serum and housed in a 5% $CO_2$ Incubator at 37° C.

For single agent $IC_{50}$ determination, cells were plated on a 96 well microplate and allowed 24 hours to adhere. Drugs were administered to the drug plate by the following: compound stock solutions (10 mM) were added to a drug plate where a 1:10 dilution was performed. Following the dilutions, 2 μl of test compound was transferred to the corresponding wells in the cell-containing 96-well plate with 198 μl of growth media. The compounds were tested over a range of 0.1 pM-100 μM for 72 hours. Following 72 hours of continuous exposure cell viability was determined by measuring the ATP activity using a commercially available cell viability assay kit. Luminescence intensity was used to relative drug activity compared to control wells and used to graphically determine the $IC_{50}$.

For combination interaction experiments, cells were plated on a 96 well microplate and allowed 24 hours to adhere. Drugs were administered to the drug plate by the following: compound stock solutions (20 mM) or combination agent stock solutions (20 mM) were added to a drug plate where a 1:10 dilution was performed. Following the dilutions, 2 μl of each VT-062 and standard agent was transferred to the corresponding wells in the cell-containing 96-well plate with 196 μl of growth media. The compound and combination agent was concurrently tested over a range of 0.1 pM-100 μM for 72 hours. Following 72 hours of continuous exposure cell viability was determined by measuring the ATP activity using a commercially available cell viability assay kit. Luminescence intensity was used to relative drug activity compared to control wells and used to graphically determine the $IC_{50}$ of combination.

Figure 3:
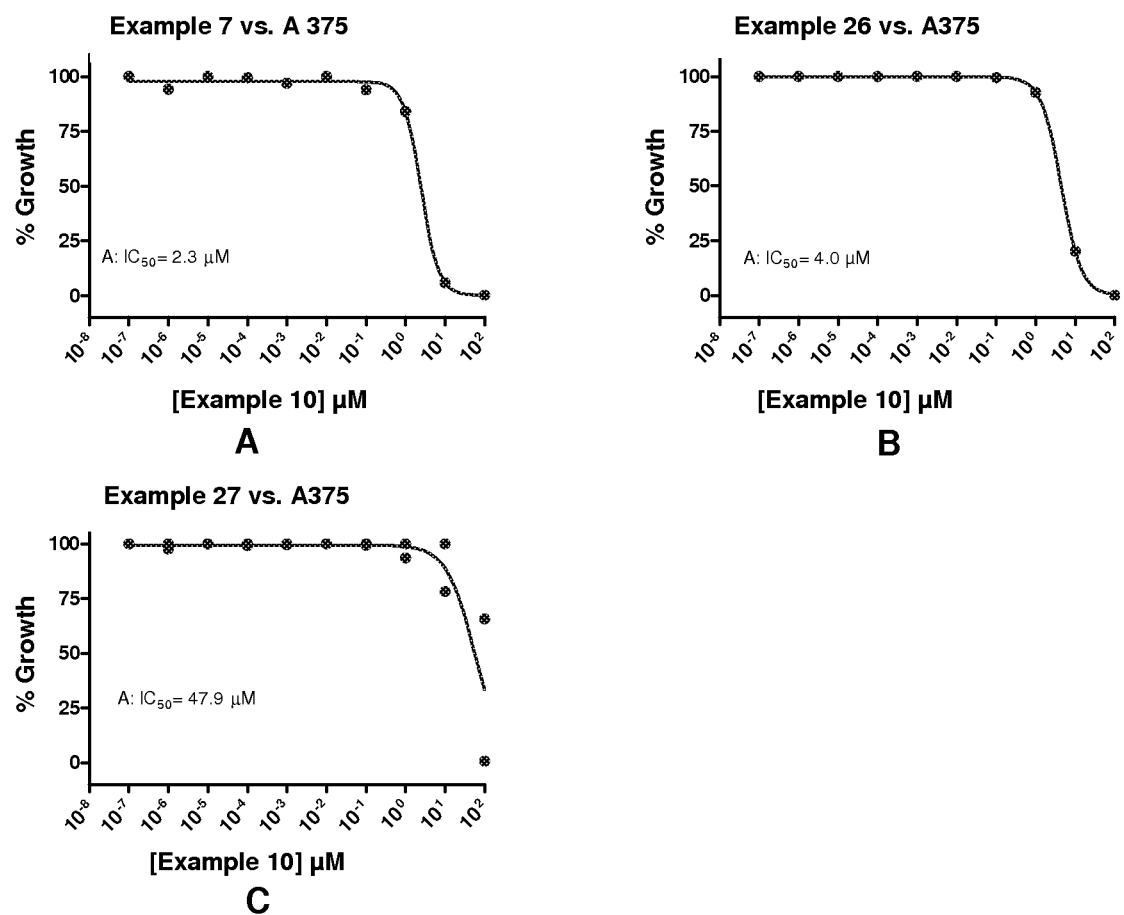
FIG. 3A depicts tumor cell inhibition by Example 7 in cell line A375.
FIG. 3B depicts tumor cell inhibition by Example 26 in cell line A375.
FIG. 3C depicts tumor cell inhibition by Example 27 in cell line A375.

FIGS. 1A, 1B, and C show that Example 10 inhibited tumor cell growth by more than 75% in the cell lines tested. FIGS. 3A, 3B, and 3C show similar tumor growth inhibition for Examples 7, 26, and 27 in A375 tumor cells.

Figure 4:
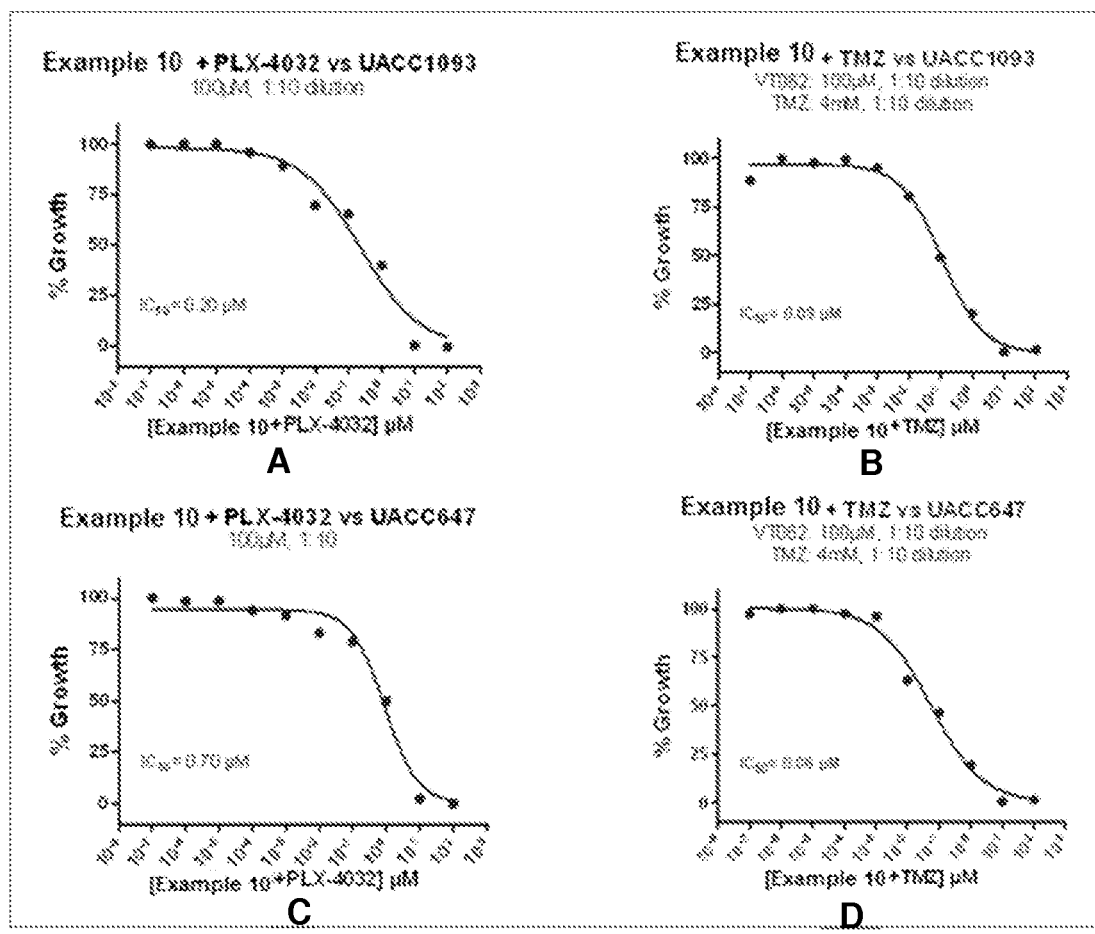
FIG. 4A depicts tumor cell inhibition by Example 10 in combination with PLX-4032 in cell line UACC1093.
FIG. 4B depicts tumor cell inhibition by Example 10 in combination with Temozolomide in cell line UACC1093.
FIG. 4C depicts tumor cell inhibition by Example 10 in combination with PLX-4032 in cell line UACC647.
FIG. 4D depicts tumor cell inhibition by Example 10 in combination with Temozolomide in cell line UACC647.

FIGS. 4A and 4C show that Example 10 in combination with PLX-4032 had a 2.6-3.25% increase in tumor growth inhibition against in combination than Example 10 alone in PLX-4032 resistant melanoma cell lines. FIGS. 4B and 4D show that Example 10 in combination with Temozolomide had a 7-30% increase in tumor growth inhibition in combination than Example 10 alone in those same cell lines.

Biological Example 2

Autophagy Inhibition Screen and Quantification

U2OS cells stably expressing ptfLC3 (Adgene plasmid 21074)(Kimura, et al., 2007) were seeded at 5,000 cells per well in 5A McCoy's medium (Invitrogen, Carlsbad, Calif.) with 10% fetal bovine serum (FBS, Invitrogen) in 96-well glass bottom tissue culture plates for 24 hours at 37° C. and 5% $CO_2$. Cells were treated with VATG compounds in a 10-point dose response for three hours, fixed with 3.7% formaldehyde, and nuclei were stained with Hoechst 33342 (Invitrogen). Cells were visualized using a 60× oil-immersion objective on a Nikon fluorescent microscope and pftLC3 fluorescence was compared with that of a DMSO vehicle control within each plate. Doses were qualitatively scored based on increased accumulation of ptfLC3 labeled punctae from zero punctae and higher.

An ED was then established for each compound. The compounds were repeated alongside chloroquine and quinacrine on U2OS cells seeded at 50,000 cells per well in 5A McCoy's with 10% FBS on number 1.5 coverglasses in 24-well tissue culture dishes. After 24 hours, the cells were treated at set doses of 0.3 uM, 1 uM, 3 uM, 10 uM, and 30 uM for three hours for confirmation. Cells were washed with 1×PBS, fixed with 3.7% formaldehyde, and nuclei were stained with Hoechst 33342 (2 ug/mL). Coverglasses were inverted onto a microscope slide using mounting gel. The microscope slides were imaged using a 60× oil-immersion objective on a Nikon Eclipse Ti fluorescent microscope and 10 images at each dose were taken for quantification. Image processing and quantification were completed with the Nikon NIS Elements software. To quantify, images were deconvoluded using a 2D blind deconvolution function with one iteration and settings of normal cell thickness and normal noise level. Regions of interest (ROI) were drawn around the edges of each cell excluding the nuclear region. Intensity thresholds were set to include all pixels equal to or greater than the intensity above the mean background fluorescence. Objects within the threshold ROIs were quantified using an automated object count function and exported to Excel (Microsoft). Although other parameters were also collected, the mean intensity of the objects was averaged between the 10 images of each dose, or approximately 35 cells. Representative images were chosen for each dose and the LUTs were set based on the mean intensity of the DMSO control. The mean intensity of each image was divided by the mean intensity of the DMSO control and the LUTs were adjusted by the percent difference to avoid viewing the background intensity.

The quantified $ED_{50}$ values are shown in Table 3.

TABLE 3

| Example | Autophagy Inhibition (ED50) |
|---|---|
| 1 | ***** |
| 2 | ***** |
| 3 | * |
| 4 | ***** |
| 5 | ***** |
| 6 | * |
| 7 | ***** |
| 8 | *** |
| 9 | * |
| 10 | ***** |
| 11 | * |
| 12 | *** |
| 13 | ***** |
| 14 | * |
| 15 | ***** |
| 16 | *** |
| 17 | *** |
| 18 | *** |
| 19 | *** |
| 20 | *** |
| 21 | ***** |
| 22 | *** |
| 23 | ***** |
| 24 | *** |
| 25 | ***** |
| 26 | ***** |
| 27 | *** |
| 28 | *** |

Biological Example 3

Human Tumor Xenograft Study

Female mice were inoculated subcutaneously in the right flank with 0.1 ml of a 50% RPMI/50% Matrigel™ (BD Biosciences, Bedford, Mass.) mixture containing a suspension of A375 Human melanoma tumor cells (approximately $5 \times 10^6$ cells/mouse).

When tumor reached approximately 130 mg, mice were randomized into treatment groups. Body weights were recorded when the mice were randomized and were taken twice per week (on Study Days 3 and 7 for each cycle) thereafter in conjunction with tumor measurements. Treatment began on the day of randomization. Example 10 was delivered orally in a vehicle consisting of 5% DMA, 10% propylene glycol, 20% PEG 400, and 65% sterile water. Example 10 was administered daily for 21 days.

Figure 5:
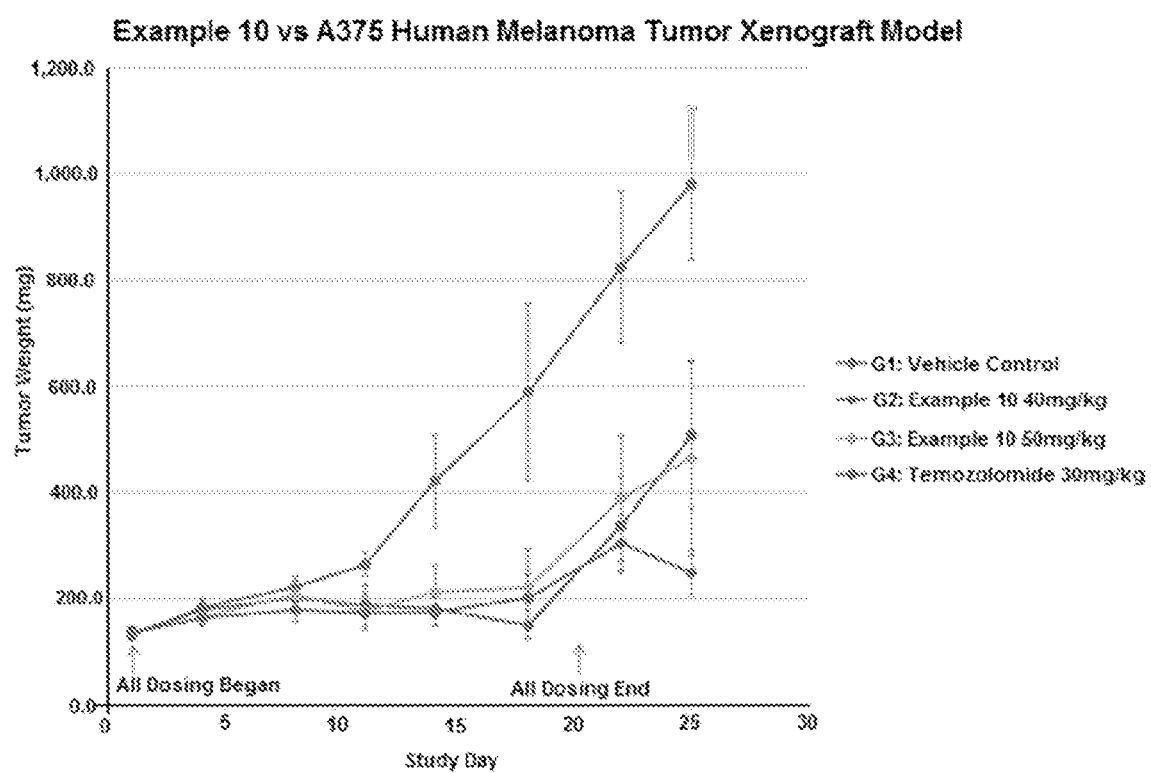
FIG. 5 depicts tumor cell weight in mice treated with Example 10.

FIG. 5 shows that tumor weight in mice over the course of 25 days. Example 10 inhibited tumor growth by greater than 50% after 25 days.

Biological Example 4

Autophagy Inhibition Screen and Quantification

Figure 6:
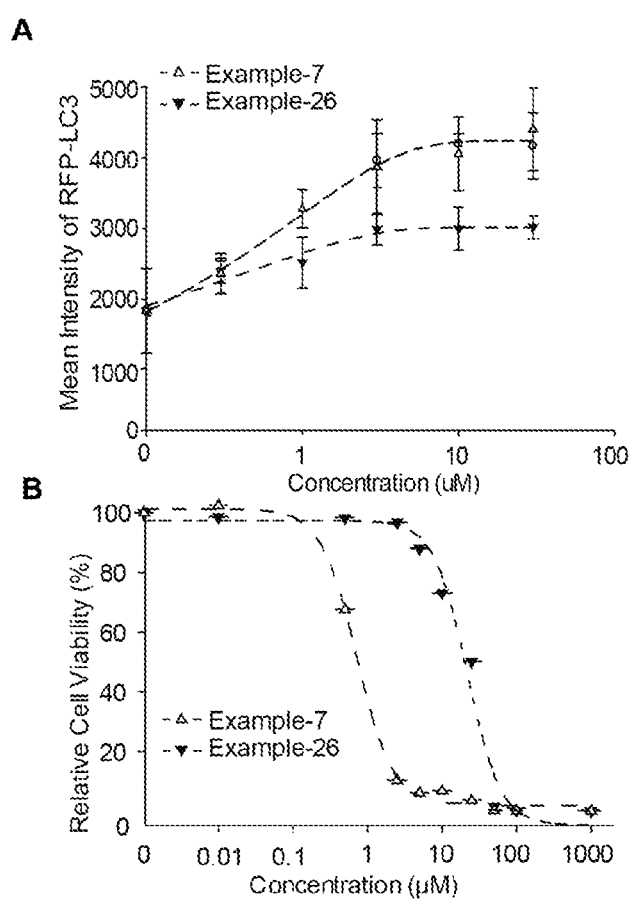
FIG. 6A depicts a graph showing mean intensity quantification of red punctae on a dose response of Example 7 and Example 26 using image analysis software.
FIG. 6B depicts a graph showing percentage of cell viability after 48 hours of treatment with Example 7 and Example 26.

U2OS cells stably expressing ptfLC3 (Adgene plasmid 21074)(Kimura, et al., 2007) were seeded at 5,000 cells per well in 5A McCoy's medium (Invitrogen, Carlsbad, Calif.) with 10% fetal bovine serum (FBS, Invitrogen) in 96-well glass bottom tissue culture plates for 24 hours at 37° C. and 5% $CO_2$. Cells were treated with compounds in a 10-point dose response for three hours, fixed with 3.7% formaldehyde, and nuclei were stained with Hoechst 33342 (Invitrogen). Cells were visualized using a 60× oil-immersion objective on a Nikon fluorescent microscope and pftLC3 fluorescence was compared with that of a DMSO vehicle control within each plate. Doses were qualitatively scored based on increased accumulation of ptfLC3 labeled punctae from zero punctae and higher. An ED was established for each compound. The compounds selected, Example 7 and Example 26, were repeated on U2OS cells seeded at 50,000 cells per well in 5A McCoy's with 10% FBS on number 1.5 coverglasses in 24-well tissue culture dishes. After 24 hours cells were treated at set doses of 0.3 uM, 1 uM, 3 uM, 10 uM, and 30 uM for three hours for confirmation. Cells were washed with 1×PBS, fixed with 3.7% formaldehyde, and nuclei were stained with Hoechst 33342 (2 ug/mL). Coverglasses were inverted onto a microscope slide using mounting gel. The microscope slides were imaged using a 60× oil-immersion objective on a Nikon Eclipse Ti fluorescent microscope and 10 images at each dose were taken for quantification. Image processing and quantification were completed with the Nikon NIS Elements software. To quantify, images were deconvoluded using a 2D blind deconvolution function with one iteration and settings of normal cell thickness and normal noise level. Regions of interest (ROI) were drawn around the edges of each cell excluding the nuclear region. Intensity thresholds were set to include all pixels equal to or greater than the intensity above the mean background fluorescence. Objects within the threshold ROIs were quantified using an automated object count function and exported to Excel (Microsoft). Although other parameters were also collected, the mean intensity of the objects was averaged between the images of each dose, or approximately 35 cells. Representative images were chosen for each dose and the LUTs were set based on the mean intensity of the DMSO control. The mean intensity of each image was divided by the mean intensity of the DMSO control and the LUTs were adjusted by the percent difference to avoid viewing the background intensity. FIG. 6A shows the mean intensities for Example 7 and Example 26.

Biological Example 5

Cell Viability ($LD_{50}$) Screen

U2OS cells were seeded at 500 cells per well in 5A McCoy's with 10% FBS in 96-well clear bottom, black-walled tissue culture plates. After 24 hour incubation, cells were treated with compounds in triplicate with a 10-point half log dose response for 24 and 48 hours. Medium was removed with 2× CellTiter Glo (Promega) reagent mixed 1:1 with optimem (Invitrogen) was added at 100 uL per well and incubated rocking at room temperature for 15 minutes. A total of 75 uL per well was moved to a white-walled 96-well plate and read using the 96 LUM program on an EnVision plate reader 0 and exported to Excel (Microsoft) for analysis. FIG. 6B shows the relative cell viabilities of Example 7 and Example 26.

Biological Example 6

Demonstrating an Inhibitory Lysosomal Mechanism of Action

To determine deacidification of the lysosome, cells were incubated with LysoTracker Red, a dye that localizes to the lysosome based on the low acidity of the compartment. If the lysosome is no longer acidic, there is a loss in the amount of LysoTracker Red staining. Lysosomal inhibition was further determined by immunofluorescence of lysosome-associated membrane protein-1 (LAMP1). If the lysosome is inhibited, lysosomal turnover should decrease and an increase in the amount of LAMP1 staining would be apparent. U2OS cells were treated with Example 7 or Example 26 at 3 μM for 3 hours, supplementing LysoTracker Red for the final hour. Example 7 and Example 26 treatments all caused substantial increases in LAMP1 staining and essentially ablated LysoTracker Red staining, indicating that the compounds inhibit lysosomal turnover through deacidification.

Using image analysis software, the mean intensities of both the LAMP1 and LysoTracker Red staining were measured and represent altered intensity level between treatments on intensity plots. Individual points were measured using a line scan on the image analysis software, which measures the intensity across the path of a line at any given point. Not only does the presence of LAMP1 positive membranes increases, but the intensity in LAMP1 staining also increases with Example 7 and Example 26 treatment. The inverse relationship in intensity holds true for LysoTracker Red staining. Treatment with Example 7 and Example 26 showed less intense LysoTracker Red staining, indicating an increase in pH.

Other Embodiments

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive.

The scope of the invention should, therefore, be determined not with reference to the above description, but should instead be determined with reference to the following appended claims, along with the full scope of equivalents to which such claims are entitled.

The invention claimed is:

1. A compound, wherein the compound is:
6-Chloro-N-(2-(4-methylpiperazin-1-yl)ethyl)-1,2,3,4-tetrahydroacridin-9-amine.

* * * * *